United States Patent
Gurule et al.

(10) Patent No.: US 11,977,723 B2
(45) Date of Patent: May 7, 2024

(54) IMAGE TILING AND DISTRIBUTIVE MODIFICATION

(71) Applicant: Palantir Technologies Inc., Denver, CO (US)

(72) Inventors: Myles Gurule, New York, NY (US); Matthew Owens, New York, NY (US)

(73) Assignee: Palantir Technologies Inc., Denver, CO (US)

(*) Notice: Subject to any disclaimer, the term of this patent is extended or adjusted under 35 U.S.C. 154(b) by 0 days.

(21) Appl. No.: 17/118,425

(22) Filed: Dec. 10, 2020

(65) Prior Publication Data

US 2021/0181930 A1 Jun. 17, 2021

Related U.S. Application Data

(60) Provisional application No. 62/949,354, filed on Dec. 17, 2019.

(51) Int. Cl.
| | |
|---|---|
| *G06F 3/04845* | (2022.01) |
| *G06F 3/04842* | (2022.01) |
| *G06T 3/40* | (2006.01) |

(52) U.S. Cl.
CPC ...... *G06F 3/04845* (2013.01); *G06F 3/04842* (2013.01); *G06T 3/40* (2013.01); *G06F 2203/04806* (2013.01)

(58) Field of Classification Search
CPC ............. G06F 3/04845; G06F 3/04842; G06F 2203/04806; G06T 3/40
See application file for complete search history.

(56) References Cited

U.S. PATENT DOCUMENTS

| | | |
|---|---|---|
| 7,158,878 B2 | 1/2007 | Rasmussen et al. |
| 8,798,394 B2 * | 8/2014 | Lett .................... G01N 21/6458 382/128 |

(Continued)

FOREIGN PATENT DOCUMENTS

| | | |
|---|---|---|
| EP | 2988277 | 2/2016 |
| EP | 3839771 | 6/2021 |

OTHER PUBLICATIONS

Official Communication for European Patent Application No. 20215238.5 dated May 18, 2021, 9 pages.

(Continued)

*Primary Examiner* — Jeremy L Stanley
(74) *Attorney, Agent, or Firm* — Knobbe, Martens, Olson & Bear, LLP

(57) ABSTRACT

A method of configuring images for display in a user interface can include accessing an image and information indicating locations of a plurality of features of interest within the image. The method can include determining a first tile arrangement indicating a first quantity of tiles associated with a first zoom level such that each of the first tiles including a portion of the image at a first downsampling such that the first tiles collectively represent the image. The method can include determining a second tile arrangement indicating a second quantity of tiles associated with a second zoom level. The method can include determining a zoom level associated with display of a portion of the image and one or more tiles associated with the portion of the image at the determined zoom level. The method can include generating the determined one or more tiles and displaying them in a browser.

20 Claims, 13 Drawing Sheets

(56) References Cited

U.S. PATENT DOCUMENTS

| | | | | |
|---|---|---|---|---|
| 8,799,799 | B1* | 8/2014 | Cervelli | G06F 16/29 715/765 |
| 9,600,146 | B2* | 3/2017 | Cervelli | G06T 11/60 |
| 9,740,957 | B2* | 8/2017 | Pauly | G06K 9/00147 |
| 9,805,248 | B2* | 10/2017 | Brieu | G06K 9/66 |
| 10,438,096 | B2* | 10/2019 | Lesniak | G06T 7/136 |
| 10,769,788 | B2* | 9/2020 | Song | G16H 80/00 |
| 2009/0221999 | A1* | 9/2009 | Shahidi | A61B 34/10 128/898 |
| 2010/0026718 | A1* | 2/2010 | Jetha | G06F 3/0481 345/647 |
| 2010/0077358 | A1 | 3/2010 | Sugaya et al. | |
| 2010/0141654 | A1* | 6/2010 | Neemuchwala | A61B 8/483 345/427 |
| 2011/0060766 | A1* | 3/2011 | Ehlke | G06F 3/04845 707/802 |
| 2011/0214050 | A1* | 9/2011 | Stambaugh | G06F 16/9537 715/234 |
| 2011/0295863 | A1* | 12/2011 | Weir | G06F 16/90328 707/754 |
| 2013/0168545 | A1* | 7/2013 | Clem | H01J 49/0463 250/288 |
| 2014/0152664 | A1* | 6/2014 | Le Meur | G06T 3/40 345/428 |
| 2014/0267671 | A1* | 9/2014 | Kenny | G06K 9/3208 348/79 |
| 2014/0270344 | A1* | 9/2014 | Krishnamoorthi | G06K 9/6211 382/103 |
| 2014/0310635 | A1* | 10/2014 | Lett | G01N 21/6458 715/771 |
| 2015/0150457 | A1* | 6/2015 | Wu | G16H 30/40 600/425 |
| 2016/0011409 | A1* | 1/2016 | Oshima | G02B 21/245 348/80 |
| 2016/0070949 | A1* | 3/2016 | Tunstall | G06K 9/0014 382/133 |
| 2017/0017069 | A1* | 1/2017 | Siegel | G01J 3/10 |
| 2017/0262984 | A1* | 9/2017 | Barnes | G06T 7/11 |
| 2017/0270346 | A1* | 9/2017 | Ascierto | G06V 20/69 |
| 2019/0073510 | A1* | 3/2019 | West | G06T 7/0012 |
| 2019/0139218 | A1* | 5/2019 | Song | G06K 9/80 |
| 2019/0350659 | A1* | 11/2019 | Wang | A61B 90/00 |
| 2020/0050331 | A1* | 2/2020 | Morrison | G06F 3/04817 |
| 2020/0075169 | A1* | 3/2020 | Lau | G16B 25/10 |
| 2020/0258223 | A1* | 8/2020 | Yip | G06T 11/00 |
| 2020/0294231 | A1* | 9/2020 | Tosun | G06T 7/0012 |
| 2020/0302223 | A1* | 9/2020 | Dutta | G06K 9/6222 |
| 2020/0305739 | A1* | 10/2020 | Getman | A61B 5/0077 |
| 2020/0327671 | A1* | 10/2020 | Arbel | G06T 7/0012 |
| 2020/0372635 | A1* | 11/2020 | Veidman | G06T 7/0012 |
| 2020/0380675 | A1* | 12/2020 | Golden | G06T 7/143 |
| 2020/0381121 | A1* | 12/2020 | Wang | G16H 30/20 |
| 2020/0388029 | A1* | 12/2020 | Saltz | G06T 7/0012 |
| 2020/0388036 | A1* | 12/2020 | Skrede | G06T 7/0012 |
| 2020/0394753 | A1* | 12/2020 | Brown | G06T 7/50 |
| 2020/0395117 | A1* | 12/2020 | Schnorr | G16H 30/20 |
| 2020/0410678 | A1* | 12/2020 | Song | G06K 9/80 |
| 2021/0004650 | A1* | 1/2021 | Frank | G06T 7/136 |
| 2021/0005308 | A1* | 1/2021 | Klaiman | G06T 7/0012 |
| 2021/0027462 | A1* | 1/2021 | Bredno | G06K 9/0014 |

OTHER PUBLICATIONS

Official Communication for European Patent Application No. 20215238.5 dated Nov. 4, 2022, 7 pages.

* cited by examiner

554 ⟶ Access an image

558 ⟶ Determine a first tile arrangement indicating a first quantity of tiles associated with a first zoom level 562 ⟶ Determine a second tile arrangement indicating a second quantity of tiles 566 ⟶ Determine a zoom level associated with display of a portion of the image 570 ⟶ Determine one or more tiles associated with the portion of the image at the determined zoom level 574 ⟶ Generate the determined one or more tiles 578 ⟶ Update the user interface to display features of interest satisfying one or more received threshold parameters

FIG. 9B

IMAGE TILING AND DISTRIBUTIVE MODIFICATION

INCORPORATION BY REFERENCE OF RELATED APPLICATIONS

This application claims the benefit under 35 U.S.C. § 119(e) of U.S. Provisional Patent Application Nos. 62/949,354, filed Dec. 17, 2019, the entire contents of which is incorporated herein by reference and made a part of this specification.

BACKGROUND

Field

The present disclosure relates to image tiling and user interfaces for visualizing and analyzing those images through a distributed network.

Description of the Related Art

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Network, software, and user interface architectures can be used to display images. However, significant inadequacies exist in current architectures, especially with regard to large image files. Raw data may be obtained and stored in a database. The raw data may be obtained from a scientific experiment, an industrial process, or from some other type of sensors. The data may be disorganized or unclear to a user and/or a computer (e.g., in a machine learning environment). The data may be associated with various data objects, and the data objects may include various properties associated with the object. However, this data may be unconnected to other relevant data objects.

BRIEF DESCRIPTION OF THE DRAWINGS

FIG. 3 shows another aspect of a graphical user interface that includes a feature analysis interface.

FIG. 9B is a flowchart showing another example method using a display system that may be implemented on a computer according to one embodiment.

DETAILED DESCRIPTION

Overview

Figure 1:
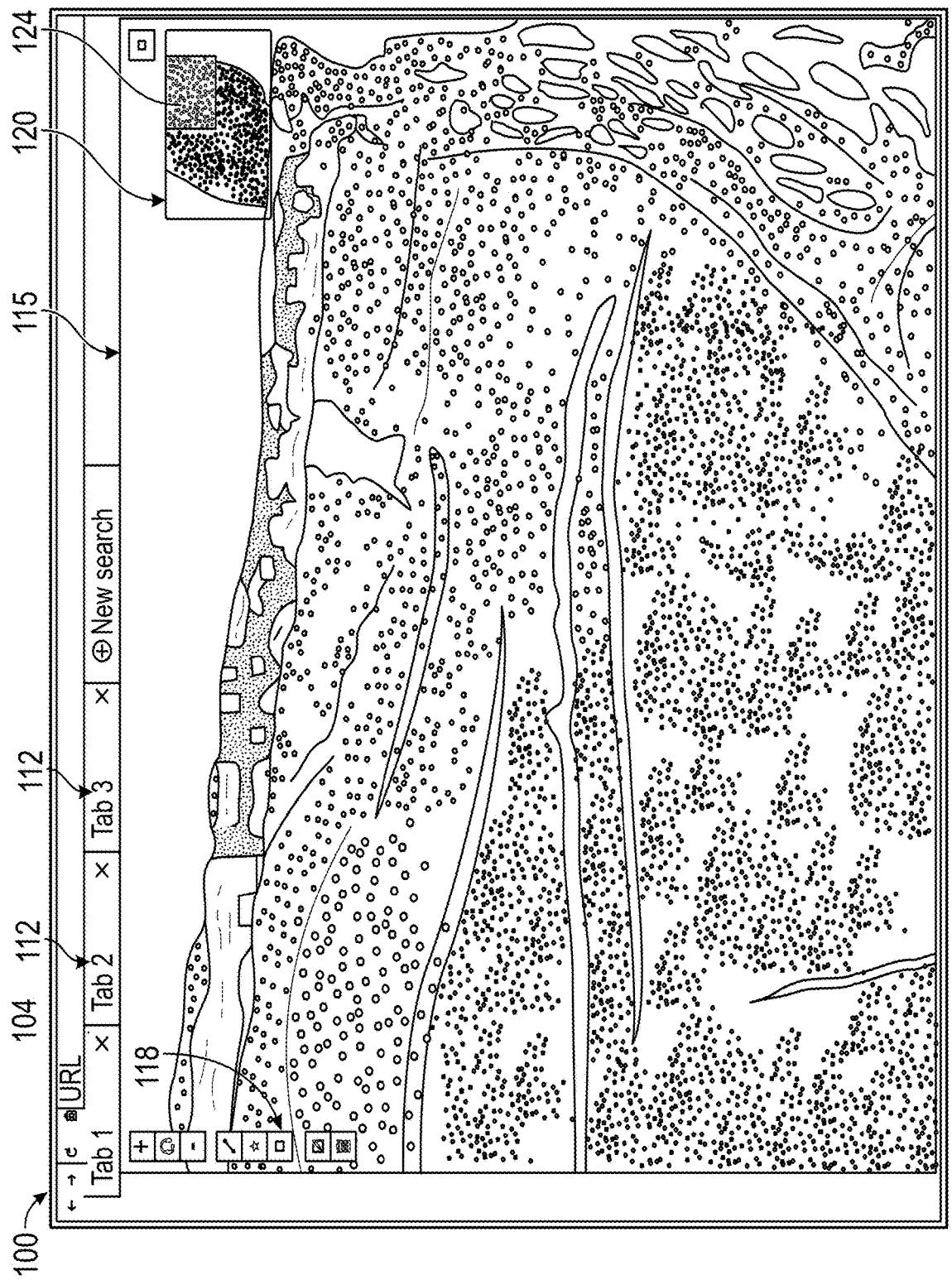
FIG. 1 shows an example graphical user interface according to one embodiment that can be displayed in a browser.

Reference will now be made in detail to example embodiments, the examples of which are illustrated in the accompanying drawings. Whenever possible, the same reference numbers will be used throughout the drawings to refer to the same or like parts.

Image data can be obtained by a sensor and stored in one or more data objects (e.g., image slices of a larger scan or mapping) that each contain a great deal of information that cannot be feasibly manipulated and/or extracted in real time due to the significant processing power that would be required. The data may come from sensors that receive medical imaging data (e.g., from an MRI, CT, or CAT scan), agricultural information (e.g., farm plot usage), and/or any other data that can be applied to a map or other spatial representation, such as a spatial map, for additional processing. Moreover, a need exists for improved user interfaces that allow one or more users (e.g., biologists, doctors, etc.) to provide further processing of the images (e.g., image slices). Such user interfaces would allow each user to supply additional information to the one or more images and for that information to be associated with the one or more images for use by other users. Thus, there is a need for user interfaces that allow a user to identify and/or isolate, for example, a concentration of features (e.g., cells, proteins, crops, etc.) within one or more of the images and to communicate that data automatically and/or remotely to a second user. Further, there is a need for a system that can adequately present a visual representation of an information-dense map that can quickly and accurately present just the right amount of information a user would find useful but also not be computationally overwhelming. Additionally, there is a need for a system that can allow such a visual representation to be manipulated and characterized by a plurality of users. Such problems are not restricted to scientific data or experimental results but may be found in any context where mapped information and images related thereto may be made.

As discussed herein, a novel user interface can allow for large image files to be condensed into chunks that allow portions of the image files to be visually represented in a real-time user interface, such as in a browser, while also presenting pertinent information a user will find helpful to identify and manipulate. A computer system can receive a plurality of images, such as medical images. Machine learning techniques can automatically identify and categorize certain features in the images. For example, machine learning may determine quantitative measures for each of a plurality of characteristics of interest in the images. In the medical image context, machine learning may be used to identify different cells of interest, such as based on protein content within the cells. In some implementations, the presence of different proteins may be part of the input image data because, for example, each image data may reflect a different protein.

Example Linking Architectures and User Interfaces

To provide a framework for the following discussion of specific systems and methods described herein, an example graphical user interface 100 will now be described with reference to FIG. 1. This description is provided for the purpose of providing an example and is not intended to limit the techniques to the example system architecture.

FIG. 1 shows an example graphical user interface 100 that can be displayed in a browser. While a "browser" is discussed herein with reference to many example implementations, other applications could be used in place of a browser, such as a proprietary image viewing application or other standalone application. The graphical user interface 100 can display an image in an image viewer interface 115. The image viewer interface 115 can include an image map 120 and/or a current view indicator 124 that identifies a portion of the image that is currently depicted in the image viewer interface 115. The image may be a high-quality and/or ultra-large data file or a portion thereof.

The example image shown in FIG. 1 represents data obtained from an immunofluorescence (IF) stain of a slice of tissue. Images obtained from other sensors are possible (e.g. chromatography, CT scan, CAT scan, X-ray, MRI, ultrasound, endoscopy, etc.). As is discussed in more detail below, the displayed image may be a portion of one or more tiles of an image. This portion may include a downsampling of image features corresponding to a currently selected zoom level for the image portion. Thus, the features that are loaded and displayed in the image viewer interface 115 are at a downsampling level that is optimized for transmission and display of relevant image data at the currently selected zoom level.

In some embodiments, the graphical user interface 100 can allow a user to navigate to the displayed image via a URL 104. Additionally or alternatively, the graphical user interface 100 can include one or more browser tabs 112 for allowing a user to access a plurality of browser elements.

The image viewer interface 115 can include one or more image interface selectors 118. As shown, the image interface selectors 118 include zoom selectors (zoom in, zoom out), pan selectors (left, right, up, down), rotation selectors (clockwise, counterclockwise), a pen annotation selector, a shape annotation selector, a box selector, a share selector, and a trash selector. The image interface selectors 118 can allow a user to annotate the image. The annotations can be saved with the image file. Thus, once a user makes annotations and saves those annotations, the annotations may be viewable by the user later and/or by a second user who views the same image file.

Figure 2:
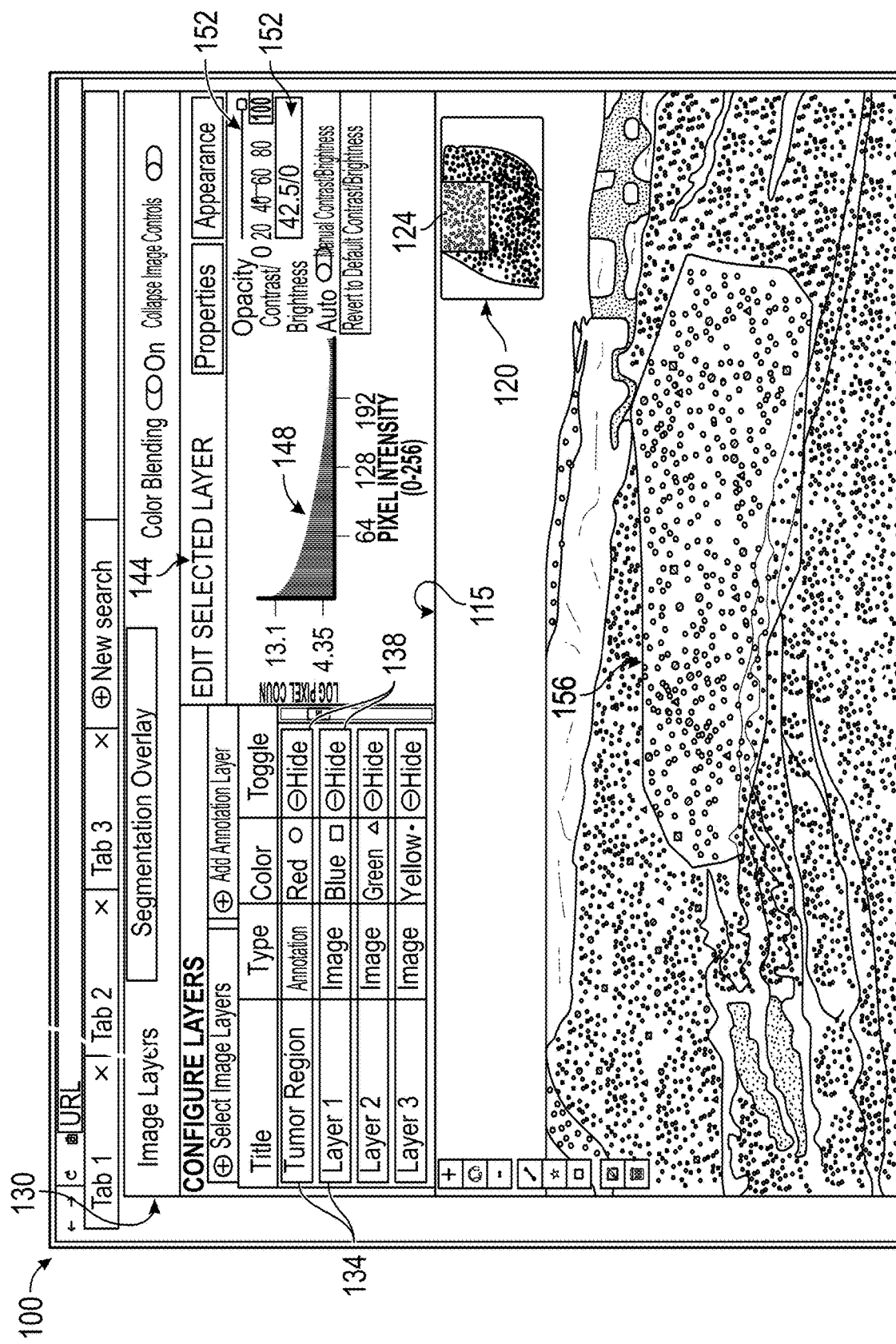
FIG. 2 shows an aspect of the example graphical user interface according to one embodiment where an example image portion annotation has been made.

FIG. 2 shows an example graphical user interface 100 where an example image portion annotation 156 has been made. As noted above, the image portion annotation 156 can be created by a user using the one or more image interface selectors 118 discussed above. The image portion annotation 156, as shown, represents a false coloring of a region of the image. The image portion annotation 156 may be a user annotation representing a tumor region of the displayed tissue portion. This image portion annotation 156 can be saved for viewing later or by another user.

Figure 6:
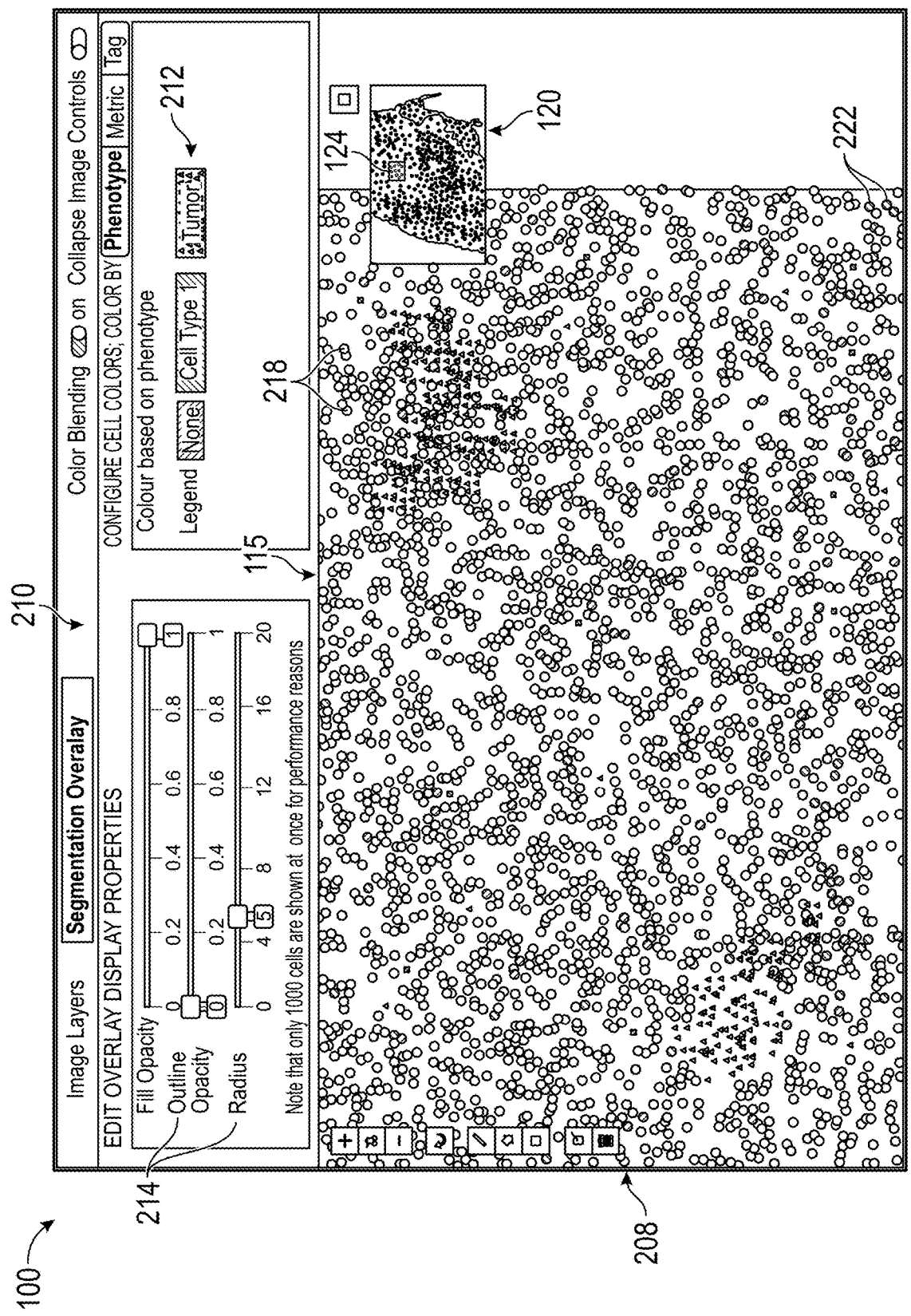
FIG. 6 shows a zoomed in view of the subregion features display of FIG. 5B within the example user interface according to one embodiment.

The graphical user interface 100 of FIG. 2 includes an image layer interface 130. The image layer interface 130 may be viewable by a user through a selection using the graphical user interface 100. For example, the user may scroll up or down in the browser. The image layer interface 130 can be selected by a selection of the "Image Layers" tab near the top of the graphical user interface 100. The image layer interface 130 displays various layer indicators 134 that indicate details of what is being shown in the image viewer interface 115. As shown, the layer indicators 134 signify that a tumor region is displayed in red (represented as larger circles in the image viewer interface 115) as an annotation. Other layers are already embedded in the image (e.g., from raw image data with false coloring applied, e.g., from machine learning algorithms) as different colors—blue, green, and yellow (represented using variously sized shapes in the image viewer interface 115). Thus, in some embodiments, raw images that are black-and-white (or grayscale) may be modified to include such false coloring. These other layers represent features of interest that can be indicated by the different colors corresponding to each respective layer, which are represented using variously sized shapes. As shown in FIG. 6, false coloring from multiple images can be blended or mixed into a single image to form a composite image. In this particular example, the features of interest correspond to proteins identified manually based on visual inspection of raw images performed on results from immunofluorescence. In some embodiments, the features of interest may be made manually from a visual inspection of output from a machine learning algorithm, manually in response to quantitative analysis, automatically through one or more machine learning algorithms, or in some other way. Thus, the various colors present an easily digestible image to a user that allow the user to identify patterns or other worthwhile aspects of the image that demand further attention or investigation. The Layers 1-3 have suggested to an expert user that the image includes a tumor region, which the user has approximately annotated as indicated by the image portion annotation 156. A user can add or remove various layers (including the annotated tumor region) using one or more corresponding image layer selectors 138.

The image layer interface 130 shown in FIG. 2 also includes a layer editing interface 144. A user can select a layer and adjust various attributes of the layer. For example, as shown the user can use a layer data indicator 148 to view a histogram of a pixel count within the image. The layer data indicator 148 displays a pixel count of pixels having a particular intensity. This information can provide a user with a graphical representation of the distribution of the layer. A user may be able to select the layer data indicator 148 to increase or decrease the pixel count proportionally across the image. The user can use layer data selectors 152 to adjust an opacity, contrast/brightness, and/or other display parameters of the layer that impact how the features of interest in layers of the composite image are blended together. Other layer data selectors 152 are possible in various embodiments.

Thresholding and Analytics

As noted above, machine learning and/or segmentation algorithms may be used to analyze image data obtained from medical imaging (e.g., CT scans, etc.) to identify cells of interest, and to generate visual data representations of the identified cells of interest that may be overlaid onto the original image. The images may be viewed in relation to visual data representations (e.g., charts, graphs, etc.), such as those illustrated in FIG. 3 (discussed below). A user can define cohorts of cells based on attributes of the cells that the machine learning segmentation has determined. This cohort information may be obtained from a manual and/or automatic inspection of the image data. For example, a user may color cells by cohort, view only cells within a cohort, and/or make further edits described herein.

A user may identify and annotate (e.g., with a marker and/or written comment) a clustering of certain cell types at a certain location within the image, while the image is displayed at a first zoom level. The user may then adjust the zoom level and/or other visual setting, and may then identify, for example, a relationship between the clustering of the cell types and a location of a portion of relevant anatomy that wasn't readily apparent in the first zoom level. In some embodiments, the segmentation outputs parameters (e.g., minimum density, minimum distance of certain features from other features, maximum concentration of a certain feature, etc.) that may be used to help identify various characteristic of cells (e.g., that the features represent cancer cells or are a particular phenotype). In some embodiments, the user interface allows the user to set and/or adjust one or more threshold associated with these parameters. For example, a threshold parameter may include a range of values, such as a range that may be selected by drawing a box around a graph or chart of displayed feature values.

The adjustments added and/or set by the user can be connected to the image for review and/or further adjustment by a different user. Additionally, combinations of characteristics may be developed by the user to generate further characteristics of images.

Figure 3:
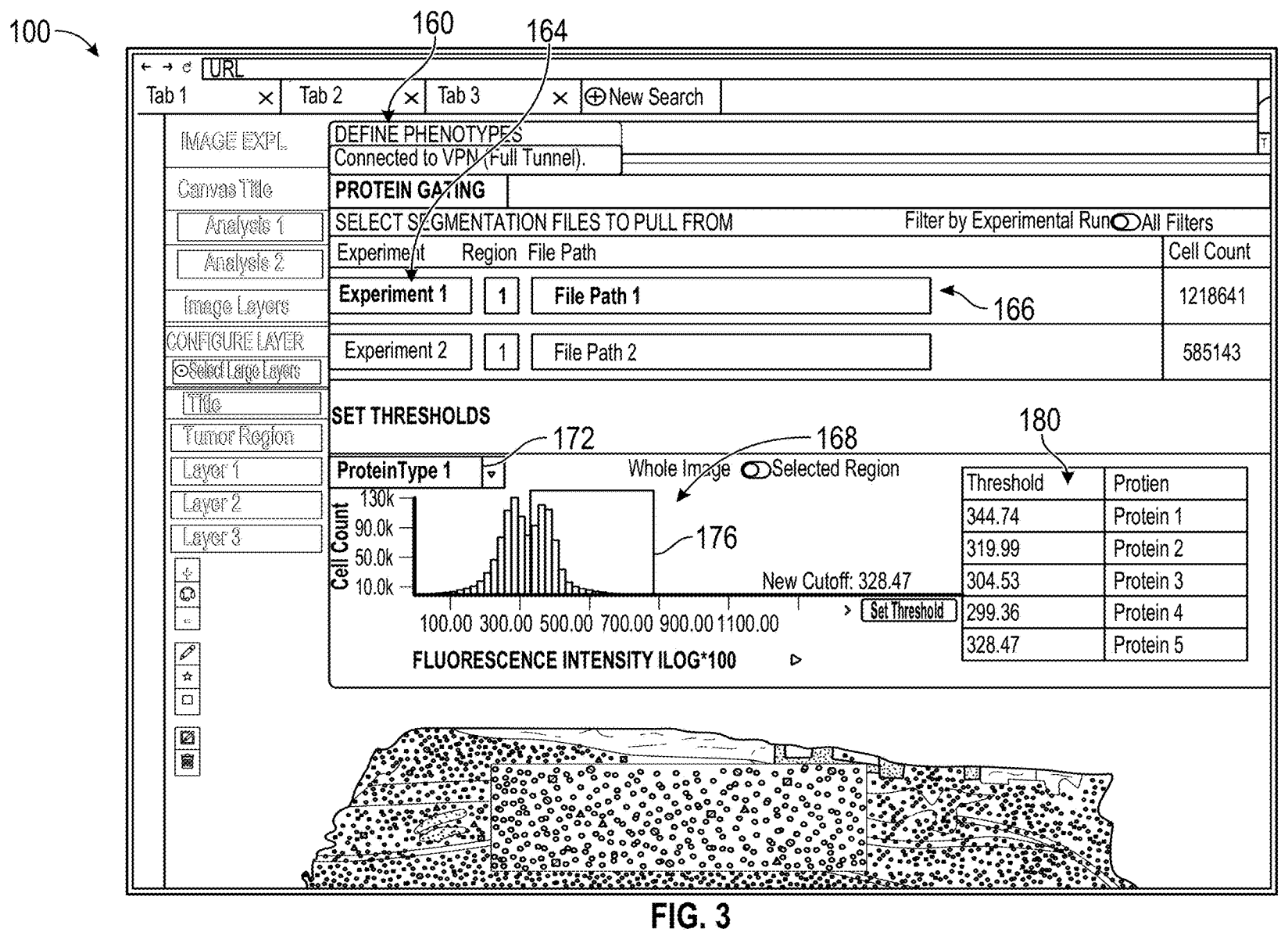

FIG. 3 shows another aspect of a graphical user interface 100 that includes a feature analysis interface 160. The feature analysis interface 160 allows a user to set one or more threshold parameters (sometimes referred to simply as "thresholds") for filtering cell parameters. The threshold parameters may include one or more of an upper threshold value, a lower threshold value, a feature type, and/or any other threshold parameter and/or filter. The threshold values may determine which features of interest are displayed based on a distribution of output values from the one or more segmentation algorithms associated with features of interest, such as an amount of protein in a cell, a distance between a cell and a nearest cell. The feature analysis interface 160 can allow a user to view the distribution of the output values associated with a selection of one or more cells (e.g., all of the cells in an image, a selected subgroup of cells, all of the cells in a selected region, etc.). The feature analysis interface 160 allows for additional analysis.

In one particular implementation, for example, a segmentation algorithm outputs quantitative properties (e.g., columns) of numbers that describe each cell. For example, a numeric representation of the amount of protein in that cell, or things like how close the cell is to its neighbors. Then, for each quantitative property, the user can view the distribution of values within the selected cells (e.g., all the cells in the image, or cells within a selected sub-region in the image). Based on the distribution, the user can define one or more thresholds, such as an upper threshold value and/or a lower threshold value.

The feature analysis interface 160 includes data source selectors 164 that indicate which sources provide the image data for the images. As shown, the data source selectors 164 indicate that the image comes from selected Region 1 of Experiment 1 and Region 1 of Experiment 2. The respective file paths are provided by corresponding data source path indicators 166.

The feature analysis interface 160 also includes a feature type analysis indicator 168 and a plurality of feature threshold indicators 180. The feature analysis interface 160 allows a user to input a feature type using the feature type selector 172. The feature type selected in FIG. 3 is a Protein Type 1.

The feature type may be a result of a machine learning algorithm or some other algorithm that takes in image data as an input and outputs quantitative values. The feature type analysis indicator 168 of FIG. 3 shows a graphical representation of the number of cells having a fluorescence intensity corresponding to the Protein Type. Other feature types can be used, depending on which features of interest are included in the image. For example, in some embodiments, the features of interest may correspond to medical features (e.g., bone densities, Alzheimer protein formations, muscle or tendon tears), agricultural features (e.g., crops in farm plots, domesticated animals in a series of fields), or other features found in an image.

The user can use the feature threshold selector 176 to select a subgroup of the features indicated in the feature type analysis indicator 168. The feature threshold selector 176 allows selection of a portion of the features by dragging across the histogram to selection a portion of the cells (e.g., as indicated with a rectangular outline in FIG. 3). In other embodiments, the selector may be a digital dial, a keyboard field, or a clickable selector (e.g., checkboxes, bars, radio buttons, etc.). The feature threshold selector 176 allows a user to fine-tune what features of interest the graphical user interface 100 displays in the image. A plurality of feature threshold selector 176 can be used one or more feature thresholds using the feature type selector 172. As shown, a user can apply the threshold parameter by clicking a "Set Threshold" button. Other configurations are possible. The feature threshold indicators 180 show which thresholds have been applied to which proteins based on the user's selections using the feature threshold selector 176. In some embodiments, the system can automatically supply one or more threshold parameters using a machine learning algorithm. For example, a group of tumor tissue may be identified by supplying the image to a trained model configured to identify tumor tissue. The system may then supply one or more of the threshold parameters and/or display them among the feature threshold indicators 180.

Figure 4:
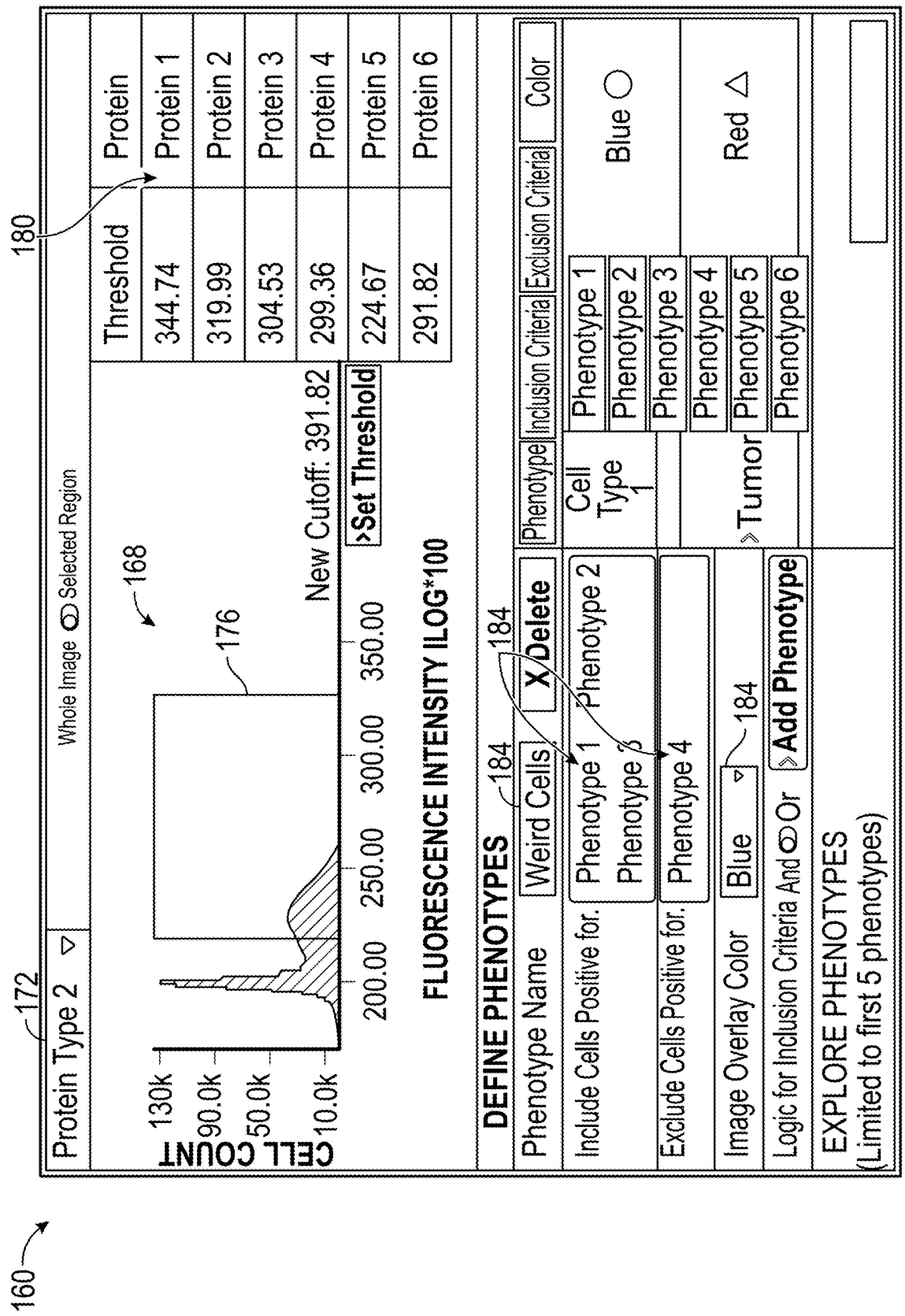
FIG. 4 shows another aspect of the feature analysis interface of the example graphical user interface according to one embodiment.

FIG. 4 shows another view of the feature analysis interface 160 where the feature type selector 172 indicates that Protein Type 2 has been selected as the feature type. Once again, a user can select a subgroup of the feature type using the feature threshold selector 176. The feature analysis interface 160 further allows a user to select other threshold parameters or filters using one or more feature group identifier selectors 184. For example, a user can define one or more phenotypes based on a selection of threshold parameters to be included or excluded. The user can select a color to be used for representing the phenotypes. The user may name a subgroup of features as a new phenotype using one of the feature group identifier selectors 184. As shown, the user has previously identified phenotypes called "Cell Type 1" and "Tumor." The user may be able to identify a characteristic of the features of interest using the feature analysis interface 160. A characteristic may generally include specific commonalities among a group (e.g., subgroup) of features and may include, for example, a protein type, a feature name, a minimum distance from a target cell or protein, etc. These features may be determined by a machine learning algorithm. In some contexts, a "subgroup" or "phenotype" may describe a group of features having a common characteristic. The characteristic can be identified by a visual indicator that identifies each feature of the subgroup. The visual indicator of the subgroup of features can include a coloring, a highlighting, a shading, and/or an outlining associated with the subgroup of features. Other configurations are possible. Thus, while threshold features are numerical, a phenotype combines the numbers in such a way that a scientific interpretation and/or explanation may be attached.

Overlaying Threshold Areas on Images

A user can select a portion or region of the image tile at the given zoom level. The selected portion can visually indicate which features meet the one or more threshold parameters. For example, if a user selects a rectangular area of the image tile, the system may display red dots for areas with features (e.g., cells) having a first characteristic (e.g., cells of a first phenotype) and may display blue dots for areas with cells having a second qualifying characteristic (e.g., cells of a second phenotype). When the user selects another region, that other region is updated with the same types of thresholding areas using the corresponding colors. As described in further detail below, various alternative implementations of the present disclosure may include additional or fewer characteristics from those described above.

Figure 5A:
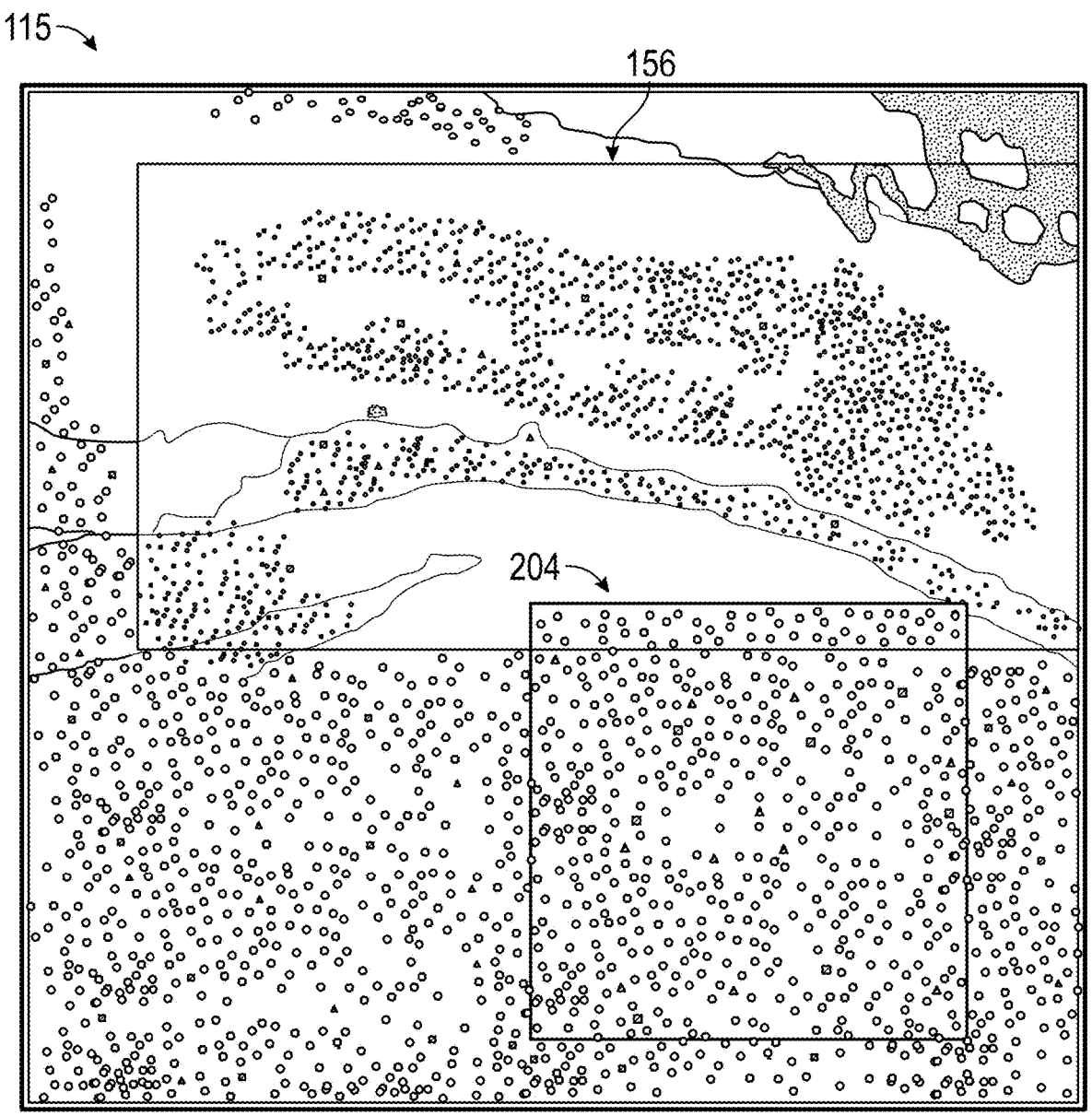
FIG. 5A shows a user selection of a portion of an image within the image viewer interface according to one embodiment.
Figure 5B:
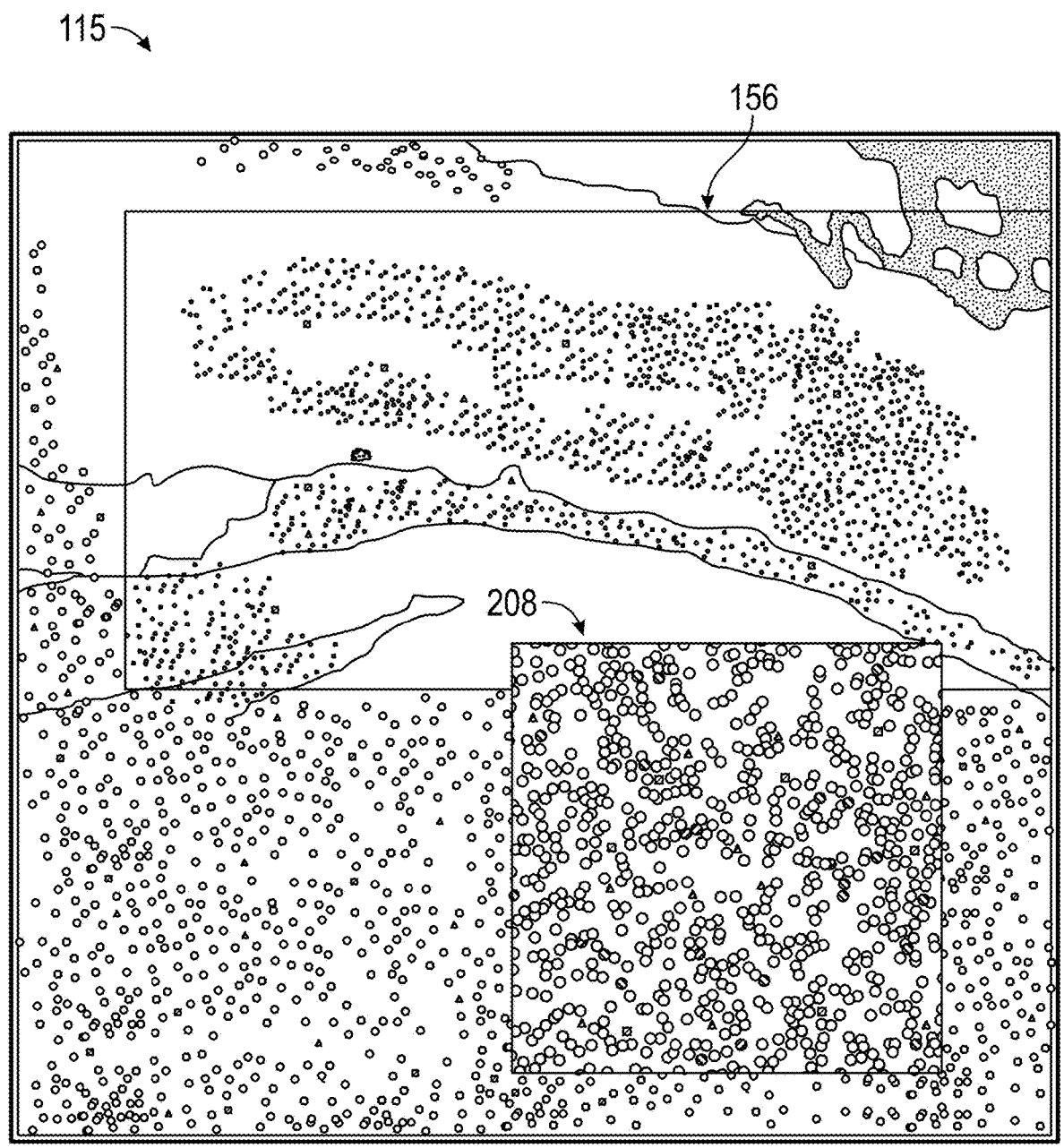
FIG. 5B shows the same image viewer interface of FIG. 5A after the selected subregion has had the selections applied to the subregion.

FIGS. 5A and 5B show a user selection of a portion of an image within the image viewer interface 115. The image viewer interface 115 can allow a user to overlay threshold areas on an image. Within the image viewer interface 115, a false coloring is shown by image portion annotation 156. A user had previously selected and annotated the image portion annotation 156. As shown in FIG. 5A, a user can also select a subregion of the image as indicated by the image subregion selector 204. The user can apply the subgroup thresholds and other display aspects (e.g., coloring, sizing, opacity, etc.). FIG. 5B shows the same image viewer interface 115 after the selected subregion has had the selections applied to the subregion. The resulting subregion features display 208 shows a plurality of features having the display characteristics indicated above with reference to FIGS. 3-4. For example, Phenotypes 1, 2, and 3 may be displayed as different colors (represented as different hatchings). The subregion features display 208 is described in more detail with respect to FIG. 6 below.

FIG. 6 shows a zoomed in view of the subregion features display 208 of FIG. 5B. The graphical user interface 100 shown also includes a feature display overlay editor interface 210, which corresponds to a "Segmentation Overlay" tab in FIG. 6. The feature display overlay editor interface 210 allows a user to further modify the display of the displayed features. Overlay selectors 214 allow a user to adjust the fill opacity, the outline opacity, and the radius of the outline. In some embodiments, additional or alternative overlay selectors 214 may be used, such as an outline type, a highlight, and/or an animation in response to a user selection (e.g., a mouse over). Other options are possible. As shown, the image viewer interface 115 shows a plurality of Tumor cell indicators 218 and Type 1 cell indicators 222, each of which correspond to a coloring indicated by a feature display overlay legend interface 212. The feature display overlay legend interface 212 shows which features (e.g., proteins, cells, phenotypes, etc.) correspond to which color aspects. A user can select a particular phenotype using the feature display overlay legend interface 212 and then can modify the display of the corresponding phenotype using the overlay selectors 214.

Example Sharing

Users may customize the look and feel of images displayed to the user, such as by modifying (e.g., tinting) an image and/or customizing artificial colors added to an image to show levels of a particular characteristic that are within a desired level. These user experience (e.g., look and feel) settings may be saved with the image and/or a larger investigation that includes the image, and used later by the user and/or other users that access the image.

In some embodiments, artificial colors are applied to an image by artificially tinting the image with a color, thereby transforming the image (rather than adding to it). In some embodiments, false coloring provides more than just a nice look and feel in the various user interfaces. The false coloring may allow analysis of images that is not possible otherwise. For example, false colors are very important when viewing more than one image layer, and allow the user to make sense of the relationship between image layers. In some embodiments, false colors are blended together to form composite colors in composite images. For example, a red tinted image layer composited with a blue tinted image layer will result in purple coloring of areas where both images have intensity.

Areas of images that are tagged and/or otherwise annotated by a user may also be save and shared with other users, such as in a cloud environment that allows real-time updates to other users that may be viewing the same image or investigation. Additionally, criteria for identifying qualifying characteristics of an image may be shared and used by other users. The tagged/annotated images can be saved and viewed by others via a browser.

Figure 7:
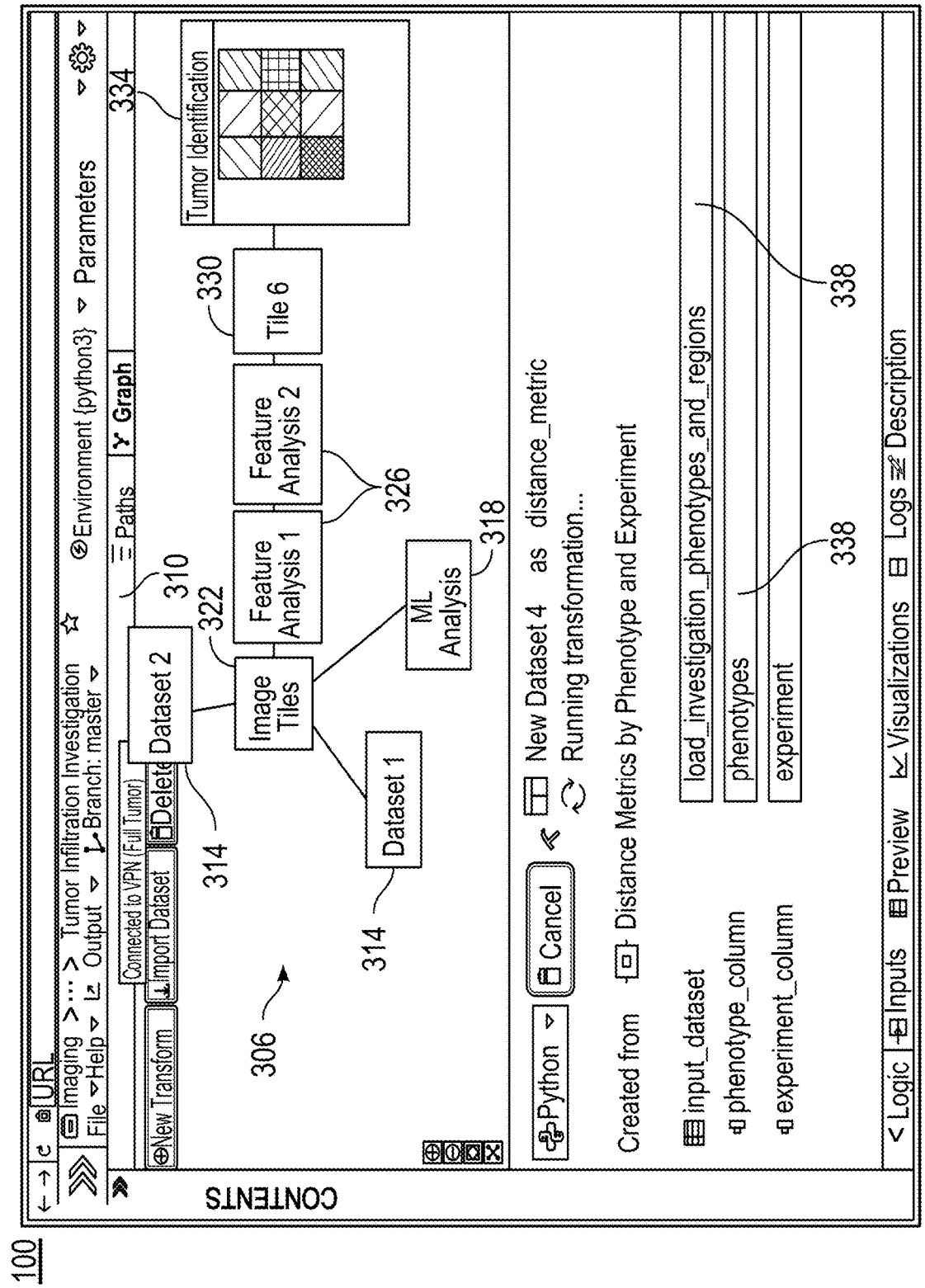
FIG. 7 shows another aspect of an example graphical user interface that allows a user to set image annotations, thresholds, and other settings to be saved and viewed separately later by the same user and/or by a separate user, according to one embodiment.

FIG. 7 shows how the image annotations, thresholds, and other settings can be saved and viewed separately later by the same user and/or by a separate user. The information that a user supplies using one or more of the interfaces described above can be linked to the underlying image file for further modification at a separate time or user interface. As noted above, one of the many benefits of the technology described herein is that in some embodiments these annotations can be stored and viewed within a browser. Thus, one or more users can view the annotations from different consoles (e.g., user interfaces) and/or at different times. In some embodiments, a plurality of users may view and/or modify the annotations simultaneously.

As shown, the graphical user interface 100 is a browser that includes a workflow analysis interface 310 for viewing and manipulating aspects of workflow 306. The workflow 306 shown includes a plurality of dataset blocks 314 representing respective datasets from which the image tiles are derived. Image tiling is described in more detail below. The dataset blocks 314 are attached to the image tiles block 322, which indicates that the data flows between the Datasets 1 and 2 and the Image Tiles. Moreover, a separate machine learning (ML) analysis is performed on the image tiles. In some embodiments, the ML analysis is performed directly on one or more underlying images before the images are tiled. In this example, the machine learning analysis block 318 is connected to the image tiles block 322, which indicates that the ML Analysis is performed on the Image Tiles. The ML Analysis can include machine learning features, such as those discussed above. For example, the Image Tiles may be analyzed by a trained model that is configured to identify features of interest within the Image Tiles. For example, the model may be trained to identify proteins, cells, cell types, phenotypes, interfaces, and/or other features. The model may be used to identify features in images related to agriculture, medicine, and/or other fields.

The workflow 306 can further include one or more feature analysis blocks 326 that represent corresponding one or more analyses that a user has provided, such as those discussed above. For example, the feature analysis can include a user's setting of a combination of one or more threshold parameters and/or filters that are associated with all of the image tiles of the image tiles block 322. These settings of threshold parameters and/or other filters can be viewable by one or more users. For example, a user could select one of the feature analysis blocks 326 to view the respective feature analysis and/or modify the feature analysis (e.g., by modifying the threshold parameters, adding/subtracting threshold parameters).

The workflow 306 includes a tile block 330 that represents a tile of the image tiles associated with the image tiles block 322. A user can select the tile block 330 to view the associated tile (Tile 6 as shown). The tile can include the associated annotations, including possible associated filters and/or threshold parameters associated specifically with that tile. The user can modify, add, and/or subtract annotations and/or threshold parameters associated with the tile. These changes can be saved and made viewable by a later different viewer (or the same viewer). In some embodiments, a selection of the tile block 330 will allow the user to view only the image itself but not the annotations.

The workflow 306 includes a display overlay block 334 that is also selectable by a user. The display overlay block 334 in this example is a heat map summarizing the analysis that has been performed. The display overlay block 334 represents different samples across the x-axis and different proteins across the y-axis. The display overlay block 334 shows a concentration of certain proteins in a particular sample. The display overlay block 334 can additionally or alternatively include user-selected overlays for viewing later. An example of such a user-selected display overlay is described above with respect to FIG. 6. A user of can select the display overlay block 334 and view at a glance the concentration of proteins in various samples and/or view the analysis previously done. The user may then modify, add, or subtract aspects in the display overlay. In this way, in some embodiments, users can collaboratively analyze an image and refine that analysis through a distributed network.

The workflow analysis interface 310 can further include one or more workflow adjustment selectors 338. The workflow adjustment selectors allow a user to select the one or more datasets to view (that may be represented, for example, by the dataset blocks 314). The user can use the workflow adjustment selectors 338 to identify particular features and/or sources of experimental data for analysis in the workflow 306.

Optimizations for Viewing Large Images in a Browser

Each image can be preprocessed for efficient data transmission at each of multiple zoom levels. For example, each image may be associated with multiple downsampled versions of the image each with a different level of detail in the downsampled images, and each being subdivided into a different quantity of tiles that together may be rendered to represent the entire image. The images corresponding to a highest zoom level (e.g., most zoomed in) may be associated with a highest quantity of tiles with a low degree of downsampling while images corresponding to a lowest zoom level (e.g., most zoomed out) will have been downsampled the most and may be associated with a lower quantity of tiles. Thus, in some embodiments, at the highest zoom level (e.g., most zoomed in), there will be a high quantity of tiles, and each tile will show a not-very-downsampled view of a small subset of the overall image, and at the lowest zoom level, there will be a small quantity of tiles, each tile will be very downsampled, and each tile will show a large section of the overall image.

When the image is viewed in a browser, for example, only those tiles for a currently rendered zoom level and portion of the image are transferred to the browser for rendering, allowing the browser to quickly render the image and also allowing the user to access all portions of the image at all zoom levels as desired. The processing required by the system is substantially lower since the level of detail that will be visually rendered corresponds only or primarily to the tile at the selected zoom level. Thus, the details (e.g., artificial coloring areas of the image at one or more zoom levels, features having a characteristic within a given and/or selected range, features satisfying some other threshold parameter) can be displayed on the fly (e.g., in real time). Additionally, the viewing user interface (e.g., a browser) can display images at various zoom levels through selective access to tiles within the particular zoom level(s) requested by the user.

Figure 8A:
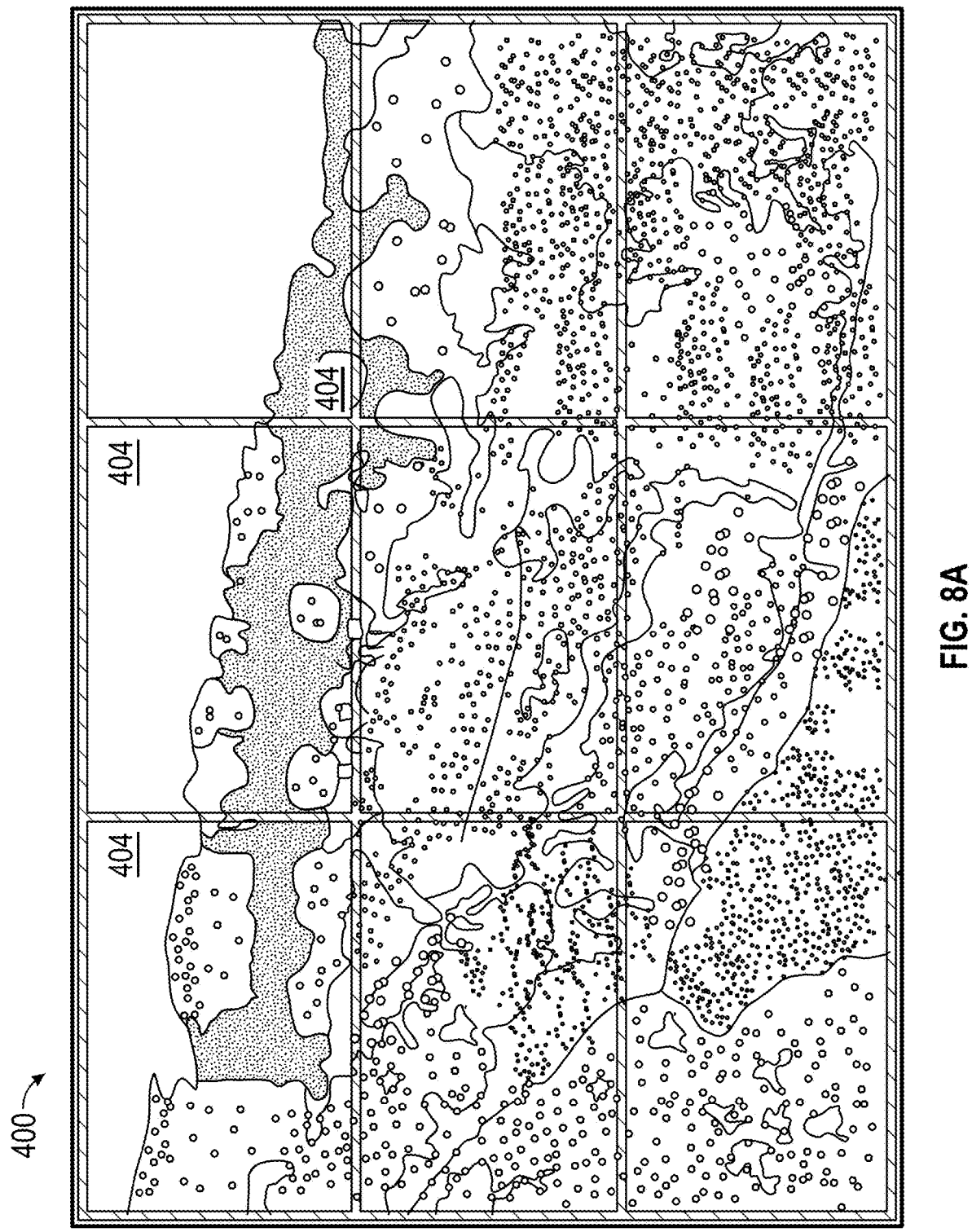
FIG. 8A shows an example image that has been tiled at a first zoom level according to one embodiment.
Figure 8B:
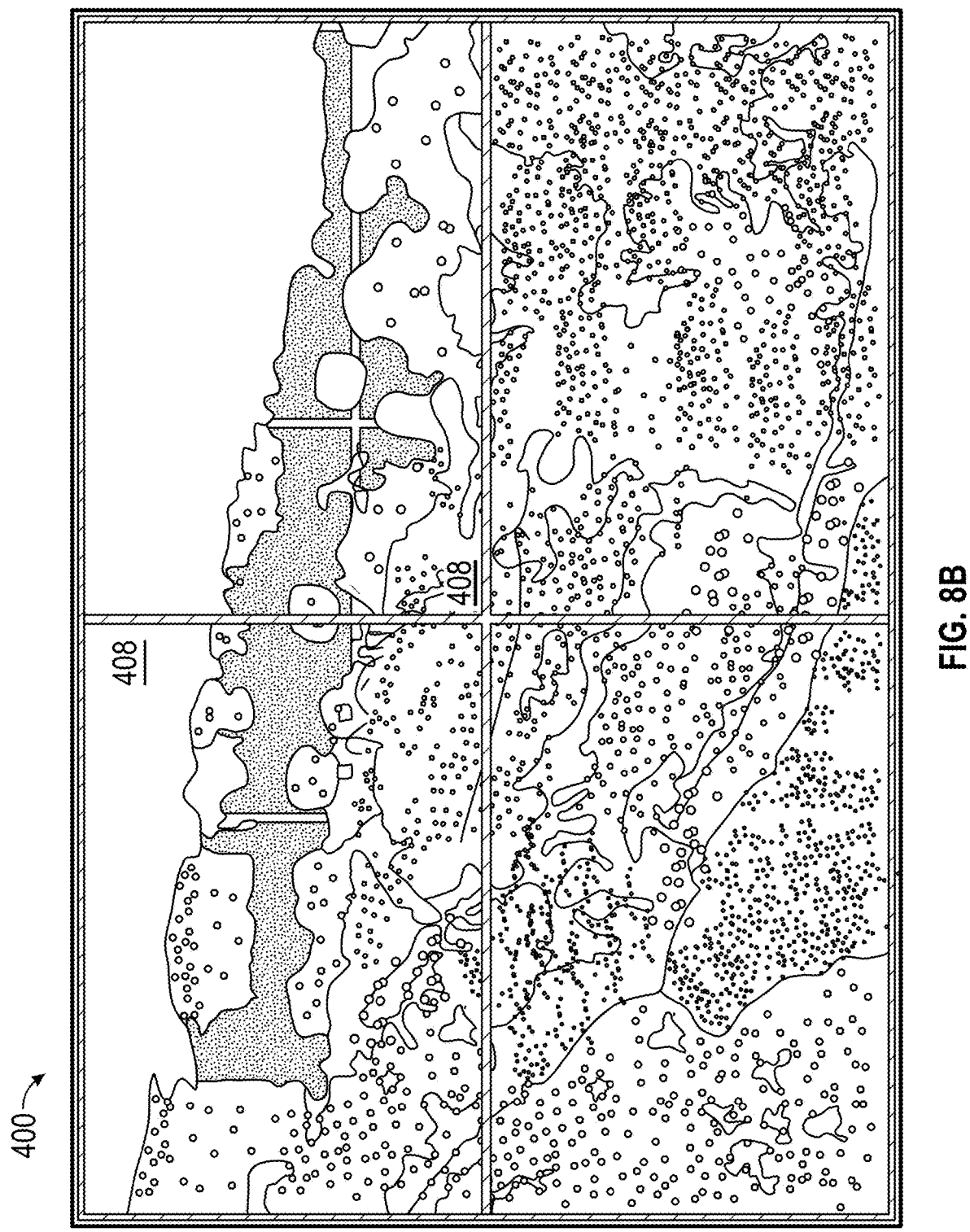
FIG. 8B shows an example image that has been tiled at a second zoom level according to one embodiment.

FIGS. 8A and 8B show example images 400 that have been tiled at two respective zoom levels. As shown in FIG. 8A, the image 400 has been tiled at a first zoom level corresponding to a plurality of first tiles 404 (shown as a 3×3 grid of tiles). In FIG. 8B, the image 400 has been tiled at a second zoom level corresponding to a plurality of second tiles 408 (shown as a 2×2 grid of tiles). In one implementation, the tiles 404 each include a higher resolution of image data than the tiles 408, while tiles 408 each include a larger area of the overall image than tiles 404. Thus, at a lower zoom level (e.g., most zoomed out), the tiles 408 may be loaded (e.g., transferred from a network server for rendering on a user device), and then when the zoom level is increased (e.g., zooming in), one or more of the tiles 404 may be loaded (e.g., transferred from the network server for rendering on a user device). In this way, not all of the tiles at all zoom levels are necessary to view various portions of the image at various zoom levels, minimizing bandwidth and processing requirements of the server and user computing systems.

The tilings shown in FIGS. 8A and 8B are only examples. For example, in one implementation at the outer most zoom level, the entire image may be rendered in a single tile, and each zoom level doubles in both dimensions, so a single tile is replaced by 4 tiles when zooming in. Various systems may be configured with different quantities of zoom levels, such as 4, 8, 10, 12, 15, 20, 22, 30 or more. An image may have additional or fewer zoom levels and/or with each zoom level having different numbers of tiles. For example, an image can have a tiling corresponding to a grid of 1×8, 1×6, 1×5, 2×3, 3×4, 3×2, 4×3, 5×4, 4×4, 5×5, 6×6, 7×7, 8×8, 9×9, 10×10, 11×11, 12×12, 13×13, 14×14, and/or other arrangement of tiles. The grid can have the same number of tiles vertically as horizontally along the image. In some embodiments, the number of tiles vertically is different from the number tiles horizontally. As shown, the first zoom level includes nine first tiles 404, and the second zoom level includes four second tiles 408. As shown, each zoom level tiles the whole image 400 and each zoom level includes tiles that are nonoverlapping. In some configurations, the tiles at a particular zoom level may overlap. In some implementations, the tiles include grayscale data and colorization of features (e.g., that are identified by one or more machine learning algorithm) may be associated with a false coloring scheme to add coloring to the tiles.

The system can create tiles on a server and transfer of the size-optimized tiles for display in the interactive user interface (e.g., the graphical user interface 100). This feature allows the system to minimize bandwidth requirements for displaying an information-dense image, which can allow for more rapid or even real-time image display. This also allows the image data to be accessed for only a portion of the image that is currently selected for display and at the current zoom level selected for display. For example, in some embodiments, the graphical user interface automatically tiles the image data all at once when an image is received at the server. Additionally or alternatively, the graphical user interface can tile the image data "on-demand" (e.g., at different zoom levels as requested by the user).

To create tiles, the system can access an image and subdivide the image into one or more groups of tiles at corresponding zoom levels. The tiles at the same zoom level may be non-overlapping. For example, system can subdivide the image into a first and second groups of non-overlapping tiles at respective first and second zoom levels. Additional or fewer zoom levels and/or groups of tiles are possible.

In some embodiments, each zoom level can be associated with a corresponding level of downsampling. The level of downsampling refers generally to the level of detail of features shown in that zoom level. As a zoom level increases (e.g., going to tiles that cover a smaller portion of the complete image), the density of detail (e.g., the number of features per unit area of the complete image) increases. Thus, a tile displaying a larger portion of the original image (zoomed out) will display a smaller feature density than a tile displaying a smaller portion of the original image (zoomed in). In this way, the system can display a suitable number of image elements rapidly without either waiting for long load times to see more detail than desired. Each image may include an enormous number of features and allowing a user to rapidly and in real time view the features allows time-sensitive information to be analyzed quickly and accurately. Moreover, this triaging of the features can allow the images to be viewed in a browser, thus allowing users to view the data from outside the internal network and/or allowing a plurality of users to view the images. A user can zoom in or zoom out on the image (e.g., using the image interface selectors 118 described above, with reference for example to FIG. 1), which can display one or more tiles of the image having a different zoom level and/or a different downsampling level. An image may be tiled to allow as many as 50 zoom levels or more.

A graphical user interface (e.g., the graphical user interface 100) can receive one or more tiles of the image from a particular zoom and/or downsampling level. The system can receive a user input representing an analysis of visual elements displayed within the one or more tiles. For example, the analysis may include setting one or more threshold parameters on various aspects of the features displayed within the one or more tiles. The threshold parameters may include, for example, setting one or more of an upper threshold value, a lower threshold value, a feature type, and/or any other threshold parameter and/or filter.

The analysis performed on the one or more tiles can be saved and associated with the tiles when they are viewed at another time and/or place. In some embodiments, the analysis can be saved and associated with every set of tiles at all zoom levels. In some embodiments, the detail of the analysis may be downsampled at a corresponding level of downsampling for each set of tiles at each zoom level. The system can allow a user to select a new zoom level (e.g., zoom out, zoom in). The system can then update the display to show one or more tiles from a different group that correspond to the area zoomed in or zoomed out. Thus, the one or more tiles at the different group will display at least some overlap of the same portion of the image before zooming in or zooming out.

The downsampling of features may change with each level of zooming in or zooming out. As noted above, cells of interested (e.g., potential tumor cells) and other features may be identified as a result of machine learning applied to the original, non-downsampled, non-tiled image. Advantageously, these identified cells of interest, along with analysis and annotations performed on the cells at any zoom level (e.g., tiles of a composite image) carry over onto every other zoom level of the image.

In some embodiments, to display the tiles, the system accesses information indicating locations of a plurality of features of interest within the image. The system may determine one or more tile arrangements indicating corresponding quantities of tiles associated with respective zoom levels. Each of the tile arrangements may include a portion of the image at a corresponding downsampling. In some embodiments, each set of tiles at a given downsampling and/or zoom level collectively represent the image. The system can determine a zoom level associated with display of a portion of the image and then determine which tiles associated with the portion of the image at the determined zoom level are to be displayed. Receipt of thresholds, analysis, annotations, etc. may be done at the determined zoom level. A user may choose to change the zoom level and/or provide additional thresholds, annotation, etc.

In an example implementation, one or more first tiles from the first zoom level may be displayed. If a user zooms out, then the system may display one or more second tiles at a second (zoomed out) zoom level. The portion of the image shown by the first tiles will have encompassed only a portion of the region of the image displayed by the second tiles at the second group (since the second tiles are at a zoomed out level). The downsampling of features is not necessarily the same and, in some cases, is different according to the level of zoom (e.g., the greater zoom level, then the greater level of detail and less downsampling). A user may provide an annotation and/or other analysis (e.g., thresholding) to the first tile. In some embodiments, the analysis done to the features displayed in the first tile tracks with the features displayed in the second tile once the user zooms out. For example, if tumor cells have been identified and/or visually annotated in the first tile, then the display of the second tile will include the identification and/or visual annotation of the tumor cells, though perhaps at a different level of detail due to a different downsampling between the two tiles. Similar functionality may apply for going from a zoomed out to a zoomed in tile.

Figure 9A:
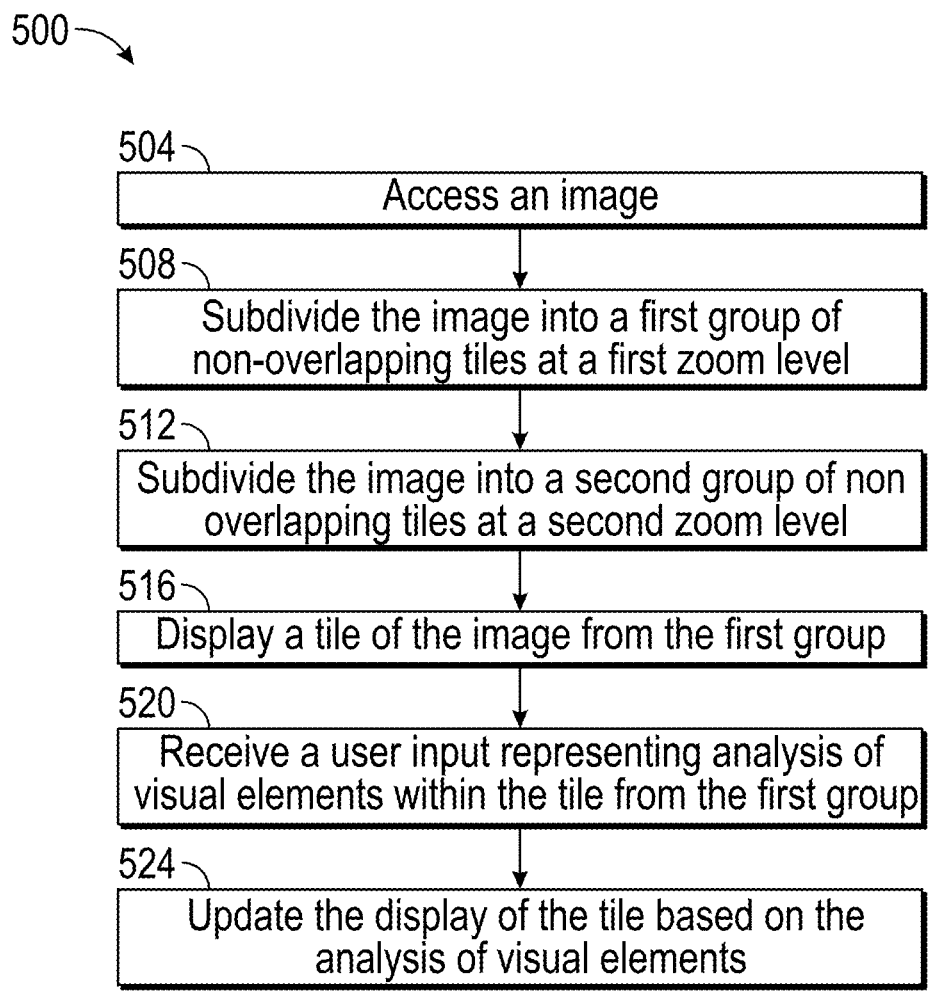
FIG. 9A is a flowchart showing an example method using a display system that may be implemented on a computer according to one embodiment.

FIGS. 9A and 9B are flowcharts illustrating two embodiments of example methods that may be implemented on a computer. Depending on the embodiment, the methods of FIGS. 9A and 9B may include fewer or additional blocks and the blocks may be performed in an order that is different than illustrated.

FIG. 9A shows an example method 500 of tiling and displaying an image with associated features of interest (or simply "features"). Beginning at block 504, a display system, for example, accesses an image. At block 508, the system subdivides the image into a first group of non-overlapping tiles at a first zoom level, and at block 512 the system subdivides the image into a second group of non-overlapping tiles at a second zoom level. For example, the system may divide the tiles into different zoom levels having corresponding different downsampling levels, such as is described with respect to FIG. 8 above. However, as noted above, in some embodiments the subdividing of the image data (e.g., blocks 508 and 512) may occur at a separate system, such as at a remote server. In some embodiments, the remote server may additionally or alternatively access the image at block 504.

At block 516, the system displays, using for example a graphical user interface, a tile of the image from the first group. At block 520, the system receives a user input representing analysis of visual elements within the tile from the first group. For example, the analysis may include setting one or more threshold parameters on various aspects of the features displayed within the tile. The threshold parameters may include setting one or more of an upper threshold value, a lower threshold value, a feature type, and/or any other threshold parameter and/or filter. The system at block 524 updates the display of the tile based on the analysis of the visual elements. In some embodiments, the system can receive a new zoom level from the user. The system can then update the display to show a tile from the second group. This tile from the second group will display at least some of the same portion of the image as the tile from the first group. For example, if the tile from the second group is more zoomed in, then the portion of the image shown by the tile at the first group will have encompassed the region of the image displayed by the tile at the second group. Alternatively, if the tile from the second group is more zoomed out, then the portion of the image shown by the tile at the first group will have encompassed only a portion of the region of the image displayed by the tile at the second group. In neither scenario is the downsampling of features necessarily the same. In some embodiments, the analysis done to the features displayed in the tile of the first group tracks with the features displayed in the tile of the second group. For example, if tumor cells have been identified and/or visually annotated in the tile of the first group, the display of the tile of the second group will include the identification and/or visual annotation of the tumor cells (though perhaps at a different level of detail due to a different downsampling between the two tiles).

FIG. 9B shows a different method 550 that a system may implement for displaying images. As shown, at block 554, the method 550 includes accessing an image (e.g., from a file). In some embodiments, the system accesses information indicating locations of a plurality of features of interest within the image, such as may have been determined using multiple machine learning algorithms applied to the image. At block 558, the method 550 includes determining a first tile arrangement indicating a first quantity of tiles associated with a first zoom level. Each of the first tiles may include a portion of the image at a first downsampling such that the first tiles collectively represent the image. At block 562, the system determines a second tile arrangement indicating a second quantity of tiles associated with a second zoom level. Each of the second tiles may include a portion of the image at a second downsampling such that the second tiles collectively represent the image. The system at block 566 determines a zoom level associated with display of a portion of the image.

At block 570 the system determines one or more tiles associated with the portion of the image at the determined zoom level and, at block 574, generates the determined one or more tiles. In some embodiments, the system receives a selection of a threshold parameter associated with one or more of the features of interest. At block 578, the method 500 includes updating the user interface to display features of interest satisfying one or more received threshold parameters (e.g., the user selection of the threshold parameter, an automatically received threshold parameter). In some embodiments, the received threshold parameters can include parameters received from a trained machine learning model.

In some configurations, the system receives the threshold parameter by receiving a minimum density, a minimum distance, a maximum number, or any combination thereof. The system may receive a user selection of a portion of the image and based on that selection, update the user interface to display results of user analytics applied to the selected portion.

In some configurations, the system, based on the selection of features and/or a subgroup of features, can identify a characteristic (e.g., cell type, protein type, feature name, minimum distance from target, etc.) relating to the selection and/or subgroup. The characteristic can be identified by a visual indicator indicating each feature of the subgroup. The visual indicator of the subgroup of features can include a coloring, a highlighting, a shading, and/or an outlining associated with the subgroup of features. Based on one or more of the selection of features, the subgroup of features, and/or the threshold parameter, the system can pass the respective selection of features, the subgroup of features, and/or the threshold parameter to a computer in communication with a second graphical user interface. In some embodiments, the second graphical user interface includes a browser. Passing the information to the second graphical user interface can allow another user to, for example, view the image with and/or without the annotations and/or modifications. In some embodiments, the method 550 includes receiving a modification (e.g., addition, subtraction, alteration) to the analysis.

The image may include one layer of a plurality of images derived from a medical scan. The method 550 can include using a trained model to automatically identifying the features of interest. The images may be obtained using one or more sensors.

Example Embodiments

Some example embodiments are provided below for illustration purposes. Additional or alternative examples are possible.

In a 1st example, a computer-implemented method for configuring images for display in a user interface comprises: accessing an image; accessing information indicating locations of a plurality of features of interest within the image; determining a first tile arrangement indicating a first quantity of tiles associated with a first zoom level, each of the first tiles including a portion of the image at a first downsampling such that the first tiles collectively represent the image; determining one or more tiles associated with the portion of the image; generating the determined one or more tiles; displaying in a user interface on a display device the generated one or more tiles; receiving selection of a threshold parameter associated with one or more of the features of interest; and updating the user interface to display features of interest satisfying the threshold parameter within the displayed one or more tiles.

In a 2nd example, the method of example 1, further comprising: determining a second tile arrangement indicating a second quantity of tiles, larger than the first quantity, associated with a second zoom level, each of the second tiles including a portion of the image at a second downsampling such that the second tiles collectively represent the image; and determining a zoom level associated with display of a portion of the image.

In a 3rd example, the method of any of examples 1-2, wherein the threshold parameter comprises one or more of a minimum density of features, a minimum distance of features from a location, a maximum number of features.

In a 4th example, the method of any of examples 1-3, further comprising: receiving a user selection of a portion of the one or more tiles; and based on the user selection the portion of the one or more tiles, updating the user interface to display a plurality of features within the portion of the one or more tiles that satisfy the threshold parameter.

In a 5th example, the method of any of examples 1-4, further comprising: determining a second zoom level associated with display of a second portion of the image, the second portion of the image having at least some portion in common with the portion of the image; determining a plurality of tiles associated with the second portion of the image at the second zoom level; generating the determined plurality of tiles; updating the user interface to display the generated one or more tiles and at least one feature of interest satisfying the threshold parameter within the displayed plurality of tiles.

In a 6th example, the method of any of examples 1-5, further comprising: receiving a user annotation within the portion of the image; storing a relationship between the position of the user annotation with the image; and passing the stored relationship to a computer for display on a second graphical user interface.

In a 7th example, the method of any of examples 1-6, further comprising: receiving a selection of features of the features of interest; and based on the selection of features, identifying a characteristic shared among all of the features of the selection of features.

In an 8th example, the method of example 6, further comprising displaying at least one of an indication of the characteristic or an indication of the selection of the features.

In a 9th example, the method of any of examples 1-8, further comprising: receiving, from a trained machine learning model, additional characteristics associated with the plurality of features; and displaying, using the user interface, the additional characteristics simultaneous with the one or more tiles.

In a 10th example, the method of any of examples 1-9, wherein the image comprises an image of a layer of tissue obtained from a medical scan.

In an 11th example, a computing system for configuring images for display in a user interface comprises: a computer readable storage medium having program instructions embodied therewith; and one or more processors configured to execute the program instructions to cause the computing system to: access an image; access information indicating locations of a plurality of features of interest within the image; determine a first tile arrangement indicating a first quantity of tiles associated with a first zoom level, each of the first tiles including a portion of the image at a first downsampling such that the first tiles collectively represent the image; determine one or more tiles associated with the portion of the image; generate the determined one or more tiles; display in a user interface on a display device the generated one or more tiles; receive selection of a threshold parameter associated with one or more of the features of interest; and update the user interface to display features of interest satisfying the threshold parameter within the displayed one or more tiles.

In a 12th example, the system of example 11, wherein execution of the one or more processors is further configured to cause the computing system to: determine a second tile arrangement indicating a second quantity of tiles, larger than the first quantity, associated with a second zoom level, each of the second tiles including a portion of the image at a second downsampling such that the second tiles collectively represent the image; and determine a zoom level associated with display of a portion of the image.

In a 13th example, the system of any of examples 11-12, wherein the threshold parameter comprises one or more of a minimum density of features, a minimum distance of features from a location, a maximum number of features.

In a 14th example, the system of any of examples 11-13, wherein the one or more processors are further configured to execute the program instructions to cause the computing system to: receive a user selection of a portion of the one or more tiles; and based on the user selection the portion of the one or more tiles, update the user interface to display a plurality of features within the portion of the one or more tiles that satisfy the threshold parameter.

In a 15th example, the system of any of examples 11-14, wherein the one or more processors are further configured to execute the program instructions to cause the computing system to: determine a second zoom level associated with display of a second portion of the image, the second portion of the image having at least some portion in common with the portion of the image; determine a plurality of tiles associated with the second portion of the image at the second zoom level; generate the determined plurality of tiles; update the user interface to display the generated one or more tiles and at least one feature of interest satisfying the threshold parameter within the displayed plurality of tiles.

In a 16th example, the system of any of examples 11-15, wherein the one or more processors are further configured to execute the program instructions to cause the computing system to: receive a user annotation within the portion of the image; store a relationship between the position of the user annotation with the image; and pass the stored relationship to a computer for display on a second graphical user interface.

In a 17th example, the system of any of examples 11-16, wherein the one or more processors are further configured to execute the program instructions to cause the computing system to: receive a selection of features of the features of interest; and based on the selection of features, identify a characteristic shared among all of the features of the selection of features.

In an 18th example, the system of example 16, wherein the one or more processors are further configured to execute the program instructions to cause the computing system to display at least one of an indication of the characteristic or an indication of the selection of the features.

In a 19th example, the system of any of examples 11-18, wherein the one or more processors are further configured to execute the program instructions to cause the computing system to: receive, from a trained machine learning model, additional characteristics associated with the plurality of features; and display, using the user interface, the additional characteristics simultaneous with the one or more tiles.

In a 20th example, the system of any of examples 11-19, wherein the image comprises an image of a layer of tissue obtained from a medical scan.

Additional Implementation Details

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure.

For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Java, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. For example, any of the processes, methods, algorithms, elements, blocks, applications, or other functionality (or portions of functionality) described in the preceding sections may be embodied in, and/or fully or partially automated via, electronic hardware such application-specific processors (e.g., application-specific integrated circuits (ASICs)), programmable processors (e.g., field programmable gate arrays (FPGAs)), application-specific circuitry, and/or the like (any of which may also combine custom hard-wired logic, logic circuits, ASICs, FPGAs, etc. with custom programming/execution of software instructions to accomplish the techniques).

Any of the above-mentioned processors, and/or devices incorporating any of the above-mentioned processors, may be referred to herein as, for example, "computers," "computer devices," "computing devices," "hardware computing devices," "hardware processors," "processing units," and/or the like. Computing devices of the above-embodiments may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In other embodiments, the computing devices may be controlled by a proprietary operating system. Conventional operating systems control and schedule computer processes for execution, perform memory management, provide file system, networking, I/O services, and provide a user interface functionality, such as a graphical user interface ("GUI"), among other things.

Figure 10:
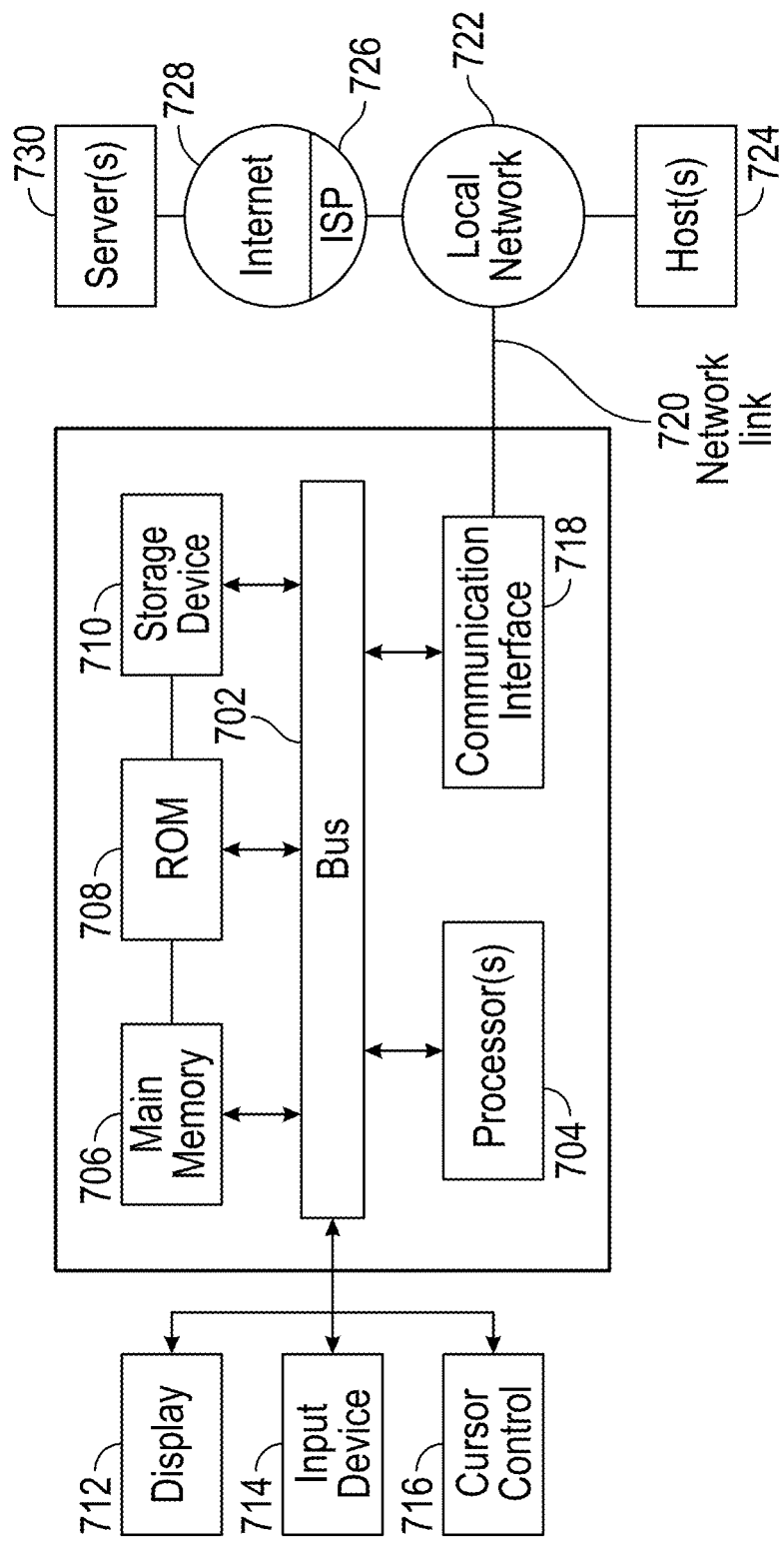
FIG. 10 is a block diagram that illustrates a computer system upon which various embodiments may be implemented according to one embodiment.

For example, FIG. 10 is a block diagram that illustrates a computer system 700 upon which various embodiments may be implemented. For example, the computer system 700 may be implemented as the graphical user interface 100 (FIG. 1) in some embodiments. Computer system 700 includes a bus 702 or other communication mechanism for communicating information, and a hardware processor, or multiple processors, 704 coupled with bus 702 for processing information. Hardware processor(s) 704 may be, for example, one or more general purpose microprocessors.

Computer system 700 also includes a main memory 706, such as a random access memory (RAM), cache and/or other dynamic storage devices, coupled to bus 702 for storing information and instructions to be executed by processor 704. Main memory 706 also may be used for storing temporary variables or other intermediate information during execution of instructions to be executed by processor 704. Such instructions, when stored in storage media accessible to processor 704, render computer system 700 into a special-purpose machine that is customized to perform the operations specified in the instructions.

Computer system 700 further includes a read only memory (ROM) 708 or other static storage device coupled to bus 702 for storing static information and instructions for processor 704. A storage device 710, such as a magnetic disk, optical disk, or USB thumb drive (Flash drive), etc., is provided and coupled to bus 702 for storing information and instructions.

Computer system 700 may be coupled via bus 702 to a display 712, such as a cathode ray tube (CRT) or LCD display (or touch screen), for displaying information to a computer user. An input device 714, including alphanumeric and other keys, is coupled to bus 702 for communicating information and command selections to processor 704. Another type of user input device is cursor control 716, such as a mouse, a trackball, or cursor direction keys for communicating direction information and command selections to processor 704 and for controlling cursor movement on display 712. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

Computing system 700 may include a user interface module to implement a GUI that may be stored in a mass storage device as computer executable program instructions that are executed by the computing device(s). Computer system 700 may further, as described below, implement the techniques described herein using customized hard-wired logic, one or more ASICs or FPGAs, firmware and/or program logic which in combination with the computer system causes or programs computer system 700 to be a special-purpose machine. According to one embodiment, the techniques herein are performed by computer system 700 in response to processor(s) 704 executing one or more sequences of one or more computer readable program instructions contained in main memory 706. Such instructions may be read into main memory 706 from another storage medium, such as storage device 710. Execution of the sequences of instructions contained in main memory 706 causes processor(s) 704 to perform the process steps described herein. In alternative embodiments, hard-wired circuitry may be used in place of or in combination with software instructions.

Various forms of computer readable storage media may be involved in carrying one or more sequences of one or more computer readable program instructions to processor 704 for execution. For example, the instructions may initially be carried on a magnetic disk or solid state drive of a remote computer. The remote computer can load the instructions into its dynamic memory and send the instructions over a telephone line using a modem. A modem local to computer system 700 can receive the data on the telephone line and use an infra-red transmitter to convert the data to an infra-red signal. An infra-red detector can receive the data carried in the infra-red signal and appropriate circuitry can place the data on bus 702. Bus 702 carries the data to main memory 706, from which processor 704 retrieves and executes the instructions. The instructions received by main memory 706 may optionally be stored on storage device 710 either before or after execution by processor 704.

Computer system 700 also includes a communication interface 718 coupled to bus 702. Communication interface 718 provides a two-way data communication coupling to a network link 720 that is connected to a local network 722. For example, communication interface 718 may be an integrated services digital network (ISDN) card, cable modem, satellite modem, or a modem to provide a data communication connection to a corresponding type of telephone line. As another example, communication interface 718 may be a local area network (LAN) card to provide a data communication connection to a compatible LAN (or WAN component to communicated with a WAN). Wireless links may also be implemented. In any such implementation, communication interface 718 sends and receives electrical, electromagnetic or optical signals that carry digital data streams representing various types of information.

Network link 720 typically provides data communication through one or more networks to other data devices. For example, network link 720 may provide a connection through local network 722 to a host computer 724 or to data equipment operated by an Internet Service Provider (ISP) 726. ISP 726 in turn provides data communication services through the world wide packet data communication network now commonly referred to as the "Internet" 728. Local network 722 and Internet 728 both use electrical, electromagnetic or optical signals that carry digital data streams. The signals through the various networks and the signals on network link 720 and through communication interface 718, which carry the digital data to and from computer system 700, are example forms of transmission media.

Computer system 700 can send messages and receive data, including program code, through the network(s), network link 720 and communication interface 718. In the Internet example, a server 730 might transmit a requested code for an application program through Internet 728, ISP 726, local network 722 and communication interface 718.

The received code may be executed by processor 704 as it is received, and/or stored in storage device 710, or other non-volatile storage for later execution.

As described above, in various embodiments certain functionality may be accessible by a user through a web-based viewer (such as a web browser), or other suitable software program). In such implementations, the user interface may be generated by a server computing system and transmitted to a web browser of the user (e.g., running on the user's computing system). Alternatively, data (e.g., user interface data) necessary for generating the user interface may be provided by the server computing system to the browser, where the user interface may be generated (e.g., the user interface data may be executed by a browser accessing a web service and may be configured to render the user interfaces based on the user interface data). The user may then interact with the user interface through the web-browser. User interfaces of certain implementations may be accessible through one or more dedicated software applications. In certain embodiments, one or more of the computing devices and/or systems of the disclosure may include mobile computing devices, and user interfaces may be accessible through such mobile computing devices (for example, smartphones and/or tablets).

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The term "substantially" when used in conjunction with the term "real-time" forms a phrase that will be readily understood by a person of ordinary skill in the art. For example, it is readily understood that such language will include speeds in which no or little delay or waiting is discernible, or where such delay is sufficiently short so as not to be disruptive, irritating, or otherwise vexing to a user.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A computer-implemented method for configuring images for display in a user interface, the method comprising:
    accessing an image;
    accessing information indicating locations of a plurality of features of interest within the image;
    determining a first tile arrangement indicating a first quantity of tiles associated with a first zoom level, each of the first tiles including a portion of the image at a first downsampling such that the first tiles collectively represent the image;
    determining one or more tiles associated with the portion of the image;
    generating the determined one or more tiles;
    displaying in a user interface on a display device the generated one or more tiles;
    displaying a graphical representation quantifying one or more of the plurality of features of interest;
    receiving, via user selection of a feature type selector, a feature type associated with the one or more of the plurality of features of interest;
    displaying, in response to the user selection of the feature type selector, an updated graphical representation quantifying the one or more of the plurality of features of interest corresponding to the selected feature type;
    receiving, within the updated graphical representation quantifying the one or more of the plurality of features of interest corresponding to the selected feature type, selection of a threshold parameter associated with the one or more of the plurality of features of interest corresponding to the selected feature type;
    updating the user interface to display features of interest satisfying the threshold parameter and corresponding to the selected feature type within the displayed one or more tiles;
    receiving, via second user selection of the feature type selector, a second feature type associated with a second of the one or more of the plurality of features of interest;
    displaying, in response to the second user selection of the feature type selector, a second updated graphical representation quantifying the second of the one or more of the plurality of features of interest corresponding to the second selected feature type;
    receiving, within the second updated graphical representation quantifying the second of the one or more of the plurality of features of interest corresponding to the second selected feature type, selection of a second threshold parameter associated with the second of the one or more of the plurality of features of interest corresponding to the second selected feature type; and
    updating the user interface to display features of interest satisfying the threshold parameter and the second threshold parameter and corresponding to the selected feature type and second feature type, respectively, within the displayed one or more tiles.

2. The method of claim 1, wherein the threshold parameter comprises one or more of a minimum density of features, a minimum distance of features from a location, a maximum number of features.

3. The method of claim 1, further comprising:
    receiving a user selection of a portion of the one or more tiles; and
    based on the user selection the portion of the one or more tiles, updating the user interface to display a plurality of features within the portion of the one or more tiles that satisfy the threshold parameter.

4. The method of claim 1, further comprising:
    determining a second zoom level associated with display of a second portion of the image, the second portion of the image having at least some portion in common with the portion of the image;
    determining a plurality of tiles associated with the second portion of the image at the second zoom level;
    generating the determined plurality of tiles; and
    updating the user interface to display the generated one or more tiles and at least one feature of interest satisfying the threshold parameter within the displayed plurality of tiles.

5. The method of claim 1, further comprising:
    determining a second tile arrangement indicating a second quantity of tiles, larger than the first quantity, associated with a second zoom level, each of the second tiles including a portion of the image at a second downsampling such that the second tiles collectively represent the image; and
    determining a zoom level associated with display of a portion of the image.

6. The method of claim 1, further comprising:
    receiving a user annotation within the portion of the image;
    storing a relationship between a position of the user annotation with the image; and
    passing the stored relationship to a computer for display on a second graphical user interface.

7. The method of claim 1, further comprising:
    receiving a selection of features of the features of interest; and
    based on the selection of features, identifying a characteristic shared among all of the features of the selection of features.

8. The method of claim 7, further comprising:
    displaying at least one of an indication of the characteristic or an indication of the selection of the features.

9. The method of claim 7, further comprising:
    receiving, from a trained machine learning model, additional characteristics associated with the plurality of features; and
    displaying, using the user interface, the additional characteristics simultaneous with the one or more tiles.

10. The method of claim 1, wherein the image comprises an image of a layer of tissue obtained from a medical scan.

11. The method of claim 1, wherein graphical representation comprises a histogram.

12. The method of claim 1, further comprising:
    receiving, via user selection of a layer selector, an image layer of a plurality of image layers associated with the generated one or more tiles, the image layer comprising associated user annotations; and displaying, in response to the user selection of the feature type selector and the layer selector, the image layer and the updated graphical representation quantifying the one or more of the plurality of features of interest corresponding to the selected feature type.

13. A computing system for configuring images for display in a user interface, the computing system comprising:
one or more a computer readable storage mediums having program instructions embodied therewith; and
one or more processors configured to execute the program instructions to cause the computing system to perform operations comprising:
accessing an image;
accessing information indicating locations of a plurality of features of interest within the image;
determining a first tile arrangement indicating a first quantity of tiles associated with a first zoom level, each of the first tiles including a portion of the image at a first downsampling such that the first tiles collectively represent the image;
determining one or more tiles associated with the portion of the image;
generating the determined one or more tiles;
displaying in a user interface on a display device the generated one or more tiles;
displaying a graphical representation quantifying one or more of the plurality of features of interest;
receiving, via user selection of a feature type selector, a feature type associated with the one or more of the plurality of features of interest;
displaying, in response to the user selection of the feature type selector, an updated graphical representation quantifying the one or more of the plurality of features of interest corresponding to the selected feature type;
receiving, within the updated graphical representation quantifying the one or more of the plurality of features of interest corresponding to the selected feature type, selection of a threshold parameter associated with the one or more of the plurality of features of interest corresponding to the selected feature type;
updating the user interface to display features of interest satisfying the threshold parameter and corresponding to the selected feature type within the displayed one or more tiles;
receiving, via second user selection of the feature type selector, a second feature type associated with a second of the one or more of the plurality of features of interest;
displaying, in response to the second user selection of the feature type selector, a second updated graphical representation quantifying the second of the one or more of the plurality of features of interest corresponding to the second selected feature type;
receiving, within the second updated graphical representation quantifying the second of the one or more of the plurality of features of interest corresponding to the second selected feature type, selection of a second threshold parameter associated with the second of the one or more of the plurality of features of interest corresponding to the second selected feature type; and
updating the user interface to display features of interest satisfying the threshold parameter and the second threshold parameter and corresponding to the selected feature type and second feature type, respectively, within the displayed one or more tiles.

14. The computing system of claim 13, wherein the threshold parameter comprises one or more of a minimum density of features, a minimum distance of features from a location, a maximum number of features.

15. The computing system of claim 13, wherein the operations further comprise:
receiving a user selection of a portion of the one or more tiles; and
based on the user selection the portion of the one or more tiles, updating the user interface to display a plurality of features within the portion of the one or more tiles that satisfy the threshold parameter.

16. The computing system of claim 13, wherein the operations further comprise:
determining a second zoom level associated with display of a second portion of the image, the second portion of the image having at least some portion in common with the portion of the image;
determining a plurality of tiles associated with the second portion of the image at the second zoom level;
generating the determined plurality of tiles; and
updating the user interface to display the generated one or more tiles and at least one feature of interest satisfying the threshold parameter within the displayed plurality of tiles.

17. The computing system of claim 13, wherein the operations further comprise:
determining a second tile arrangement indicating a second quantity of tiles, larger than the first quantity, associated with a second zoom level, each of the second tiles including a portion of the image at a second downsampling such that the second tiles collectively represent the image; and
determining a zoom level associated with display of a portion of the image.

18. The computing system of claim 13, wherein the operations further comprise:
receiving a user annotation within the portion of the image;
storing a relationship between a position of the user annotation with the image; and
passing the stored relationship to a computer for display on a second graphical user interface.

19. The computing system of claim 13, wherein the operations further comprise:
receiving a selection of features of the features of interest; and
based on the selection of features, identifying a characteristic shared among all of the features of the selection of features.

20. The computing system of claim 19, wherein the operations further comprise:
displaying at least one of an indication of the characteristic or an indication of the selection of the features.

* * * * *